United States Patent
Lorberboum-Galski et al.

(10) Patent No.: US 6,531,133 B1
(45) Date of Patent: Mar. 11, 2003

(54) PSEUDOMONAS EXOTOXIN-MYELIN BASIC PROTEIN CHIMERIC PROTEINS

(75) Inventors: Haya Lorberboum-Galski, Jerusalem (IL); Ida Steinberger, Jerusalem (IL); Eveline Beraud, Marseille (FR); Irina Marianovsky, Jerusalem (IL); Shai Yarkoni, Kfar-Saba (IL)

(73) Assignee: Yissum Research Development Company of the Hebrew University of Jerusalem (IL)

( * ) Notice: Subject to any disclaimer, the term of this patent is extended or adjusted under 35 U.S.C. 154(b) by 0 days.

(21) Appl. No.: 09/077,028

(22) PCT Filed: Nov. 17, 1996

(86) PCT No.: PCT/IL96/00151

§ 371 (c)(1),
(2), (4) Date: Jan. 27, 1999

(87) PCT Pub. No.: WO97/19179

PCT Pub. Date: May 29, 1997

(30) Foreign Application Priority Data

Nov. 17, 1995 (IL) ................................................ 116044
Dec. 26, 1995 (IL) ................................................ 116559

(51) Int. Cl.[7] .............................................. A01N 65/00

(52) U.S. Cl. ................................ 424/197.11; 424/236.1; 424/184.1; 424/192.1; 424/193.1; 424/194.1; 424/234.1; 424/260.1; 424/185.1; 424/810; 435/320.1; 514/903; 514/885; 536/23.1; 536/23.4; 536/23.7; 530/868

(58) Field of Search ....................... 424/184.1, 185.1, 424/192.1, 193.1, 194.1, 197.11, 234.1, 235.1, 236.1, 260.1, 810; 435/320.1; 514/903, 885; 536/23.1, 23.4, 23.7; 530/868

(56) References Cited

U.S. PATENT DOCUMENTS

| 3,849,550 A | | 11/1974 | Teitelbaum et al. ............. 424/78 |
| 4,767,621 A | * | 8/1988 | Jansen et al. .................. 424/85 |
| 5,182,109 A | * | 1/1993 | Tamura et al. ................. 424/92 |

(List continued on next page.)

FOREIGN PATENT DOCUMENTS

| WO | 90/12592 | | 11/1990 |
| WO | 91/18018 | | 11/1991 |
| WO | 93/21222 | | 10/1993 |
| WO | 9510301 | * | 4/1995 |

OTHER PUBLICATIONS

Roberge, Francois et al., "Selective immunosuppression of activated t cells with the chimeric toxin IL\2PE40.", Journal Of Immunology, vol. 143, No. 11, pp. 3498–3502 (1989).

(List continued on next page.)

Primary Examiner—Lynette R. F. Smith
Assistant Examiner—Ginny Allen Portner
(74) Attorney, Agent, or Firm—Browdy and Neimark, PLLC

(57) ABSTRACT

A chimeric protein comprising a *Pseudomonas aeruginosa* exotoxin (PE) moiety linked to a myelin basic protein (MBP) moiety is disclosed. The MBP moiety is selected from the group comprising: (a) MBP; (b) amino acids 69–88 of guinea-pig myelin basic protein or an antigenic portion thereof; (c) amino acids 84–102 of human myelin basic protein or an antigenic portion thereof; (d) amino acids 143–168 of human myelin basic protein or an antigenic portion thereof; and (e) an amino acid sequence in which one or more amino acids have been deleted, added, substituted or mutated in the amino acid sequences of (a), (b), (c) or (d), the modified sequence of (e) retaining at least 75% homology with the amino acid sequences of (a), (b), (c) or (d), respectively. Each of the MBP moieties of (b), (c) and (d) are linked to the PE moiety by a pentapeptide linker repeated 1–3 times. The chimeric protein is useful in treating autoimmune diseases, and especially multiple sclerosis.

14 Claims, 17 Drawing Sheets

U.S. PATENT DOCUMENTS

| | | | | |
|---|---|---|---|---|
| 5,468,481 A | * | 11/1995 | Sharma et al. | 424/125.1 |
| 5,571,499 A | * | 11/1996 | Haflet et al. | 414/43 |
| 5,571,500 A | * | 11/1996 | Haflet et al. | 424/43 |
| 5,681,571 A | * | 10/1997 | Holmgren et al. | 424/236.1 |
| 5,734,023 A | * | 3/1998 | Nag et al. | 530/403 |
| 5,759,546 A | * | 6/1998 | Weinberg et al. | 424/179.1 |
| 5,824,315 A | * | 10/1998 | Nag | 424/195.11 |
| 5,858,364 A | * | 1/1999 | Weiner et al. | 424/184.1 |
| 5,869,054 A | * | 2/1999 | Weiner et al. | 424/184.1 |
| 5,935,577 A | * | 8/1999 | Weiner et al. | 424/184.1 |
| 6,007,820 A | * | 12/1999 | Nag | 424/193.1 |
| 6,045,796 A | * | 4/2000 | Sriram et al. | 424/185.1 |

OTHER PUBLICATIONS

Martin, Roland et al., "A myelin basic protein peptide is recognized by cytotoxic cells in the context of four HLA–DR types associated with multiple sclerosis.", Journal Of Experimental Medicine, vol. 173, pp. 19–24 (1991).

Valli, Antonietta et al., "Binding of myelin basic protein peptides to human histocompatibility leukozyte antigen class II molecules and their recognition by T cells from multiple sclerosis patients.", Journal Clinical Investment, vol. 91, pp. 616–628 (1993).

Steinberger, Ida et al., "Antigen–toxin chimeric proteins–:novel agents for targeted immunotherapy of an autoimmune disease of the central nervous system.", Journal Of Meuroimmunology (1991).

Aharoni, R., et al., "Immunodulation of Experimental Allergic Encephalomyelitis by Antibodies to the Antigen–la Complex," Nature 351:147–150 (1991).

Sharma, S.D., et al., "Antigen–specific Therapy of Experimental Allergic Encephalomyelitis by Soluble Class II Major Histocompatibility Complex–peptide Complexes," Proc. Natl. Acad. Sci. U.S.A. 88:11465–11469 (1991).

Offner, H. Hashim, et al., "t–cell Receptor Peptide Therapy Triggers Autoregulation of Experimental Encephalomyelitis," Science 251:430–432 (1991).

Smilek, D.E., et al., "A Single Amino Acid change in a MYelin Basic Protein Peptide Confers the Capacity to Prevent Rather than Induce Experimental Autoimmune Encephalomyelitis," Proc. Natl. Acad. Sci. U.S.A. 88:9633–9637 (1991).

Lorberboum–Galski, H., et al., "Cytotoxic Activity of an Interleukin 2–Pseudomonas Exotoxin Chimeric Protein Produced in Escherichia coli," Proc. Natl. Acad. Sci. U.S.A. 85:1922–1926 (1988).

Ogata, M., et al., "Cytotoxic Activity of a Recombinant Fusion Protein Between Interleukin 4 and Pseudomonas Extotoxin," Proc. Natl. Acad. Sci. U.S.A. 88:4215–4219 (1989).

Siegall, C.B., et al., "Cytotoxic Activity of an Interleukin 6–Pseudomonas Exotoxin Fusion Protein on Human Myeloma Cells," Proc. Natl. Sci. U.S.A. 85:9738–9742 (1988).

Chaudhary, V.K., et al., "Selective Killing of HIV–infected Cells by Recombinant Human CD4–Pseudomonas Exotoxin Hybrid Protein," Nature 335:369–372 (1988).

Siegall, C.B., et al., "Functional Analysis of Domains II, Ib, and III of Pseudomonas Exotoxin," J. Biol. Chem. 264:14256–14261 (1989).

Kreitman, R.J., et al., "The Recombinant Immunotoxin anti–Tac(Fv)–Pseudomonas Exotoxin 40 is Cytotoxic Toward Peripheral Blood Malignant Cells from Patients with Adult T–cell Leukemia," Proc. Natl. Acad. U.S.A. 87:8291–8295 (1990).

Waldmann, T.A., "The IL–2/IL–2 receptor System: A Target for Rational Immune Intervention," Immunol. Today 14:264–270 (1995).

Wall, J.R., et al., "Peripheral Blood and Intrathyroidal Mononuclear Cell Populations in Patients with Autoimmune Thyroid Disorders Enumerated Using Monoclonal Antibodies," J. Clin. Edocrinol. Metab. 56:164–168 (1983).

Bottazzo, G.F., et al., "In Situ Characterization of Autoimmune Phenomena and Expression of HLA Molecules in the Pancreas in Diabetic Insulitis," N. Engl. J. Med. 313:353–360 (1985).

Lemm, G., et al., "Evidence for Enhanced Interleukin 2 (IL–2) Secretionand IL–2 Receptor Presentation by Synovial Fluid Lymphocytes in Rheumatoid Arthritis," Clin. Exp. Immunol. 64:71–79 (1986).

Selby, W.S., et al., "Intestinal Lymphocyte Subpopulations in Inflammatory Bowel Disease: An Analysis by Immunohistological and Cell Isolation Techniques," GUT 25:32–40 (1984).

Shapiro, M.E., et al., "Monoclonal Anti–IL–2 Receptor Antibody in Primate Renal Transplantation," Transplant Proc. 19:594–598 (1987).

Heidecke, C.D., et al., "Interactions Between T Lymphocyte Subsets Supported by Interleukin 2–Rich Lymphokines Produce Acute Rejection of Vascularized Cardiac allografts in T Cell Deprived Rats," J. Immunol. 133:582–588 (1984).

Bailon, P., et al., "Purification and Partial Characterization of and Interleukin 2–Pseudomonas Exotoxin Fusion Protein," Biotechnol. 6:1326–1929 (1988).

Casem J.P., et al., "Chimeric Chtotoxin Il–2–PE40 Delays and Mitigates Adjuvant–induced Arthritis in Rats," Proc. Natl. Acad. Sci. U.S.A. 86:287–291 (1989).

Lorberboum–Galski, H., et al., "Cardiac Allograft Survival in Mice Treated with IL–2–PE40," Proc. Natl. Acad. Sci. U.S.A. 86:1008–1012 (1989).

Kozak, R.W., et al., "IL–2–PE40 Prevents the Development of Tumors in Mice Injected with IL–2 Receptor Expressing EL4 Transfectant Tumor Cells," J. Immunol. 145–2766–2771 (1990).

Herbort, C.P., et al., "Treatment of Corneal Allograft Rejection with the Cytotoxin IL–2–PE40," Transplantation 52:470–474 (1991).

Beraud, E., et al., "Immunospecific Suppression of Encephalitogenic–Activated T Lymphocytes by Chimeric Cytotoxin IL–2–PE40," Cellular Immunol. 133:379–389 (1991).

Rose, J.W., et al., "Chimeric Cytotoxin IL2–PE40 Inhibits Relapsing Experimental Allergic Encephalomyelitis," J. Neuroimmunol. 32:209–217 (1991).

Lorberboum–Galsky, H., et al., "IL2–PE66 (4Glu), a New Chimeric Protein Cytotoxic to Human–activated T Lymphocytes," Journal Of Biological Chemistry 265–27:16311–16317 (1990).

Kibler, R.F. et al., "Immune Response of Lewis Rats to Peptide C1 (Residues 68–88) of Guinea Pig and Rat Myelin Basic Proteins," J. Exp. Med. 146:1323–13331 (1977).

Ota, K., et al., "T–cell Recognition of an Immunodominant Myelin Basic Protein Epitope in Multiple Sclerosis," Nature 346:183–187 (1990).

Fishman, A. et al., "Increased Cytotoxicity in Interleukin 2–Pseudomonas Exotoxin (IL2–PE) Chimeric Proteins Containing a Targeting Signal for Lysosomal Membranes," *Biochemistry* 33:6235–6243 (1994).
Roach, A., et al., "Characterization of Cloned cDNA Representing Rat Myelin Basic Protein: Absence of Expression in Brain of Shiverer Mutant Mice," *Cell* 34:799–806 (1983).
Collier, R.J., et al., "Structure and Activity of Diphteris Toxin," *J. Biol. Chem.* 256:1496–1503 (1971).
Gery, I., et al., "In Progress in Retinal Research," edited by Osborne, N., et al., Pergamon, Oxford and New York 5:75–109.
Swiss–Prot accession No. P02686 and Features table for variants.*
Bray, PF et al, Neurology, Sep. 1992, vol. 42(9), apges 1798–1804.*
Caamano, CA et al, FEBS Letters, vol. 252(1–2, apges 88–90, Jul. 1989.*
Deibler, GE et al, Journal of Chromatography, vol. 326, pp. 433–442, Jun. 1985.*
Domenighini, M et al, Molecular Microbiology, vol. 14(1), apges 41–50, Oct. 1994.*
Domenighini, M et al, Molecular Microbiology, vol. 5(1), pp. 23–31, Jan. 1991.*
Fors et al, Journal of Neurochemistry, vol. 60(2), pp. 513–521, Feb. 1993.*
Hashim, G.A et al, Journal of Immunology, vol. 116(1), pp. 126–130, Jan. 1976.*
Jahnke, U et al, Science, vol. 229(4710), pp. 282–284, Jul. 1985.*
Lin et al, Comparative Biochemistry and physiologyl, vol. 91(3), pp. 505–509, 1988.*
Lobet, Y et al, Infection and Immunity, vol. 59(9), pp. 2870–2879, Sep. 1991.*
Mentabery, A et al, Proceedings of National Academy of Sciences (USA), pp. 111–1114, vol. 83(4), Feb. 1986.*
Pribyl, TM et al, Proc. Natl. Acad. Sci (USA), vol. 90, pp. 10695–10699, Nov. 1993.*
Stoner, GL, Journal of Neurochemistry, vol. 55(4), pp. 1404–1411, Oct. 1990.*
Thompson, RJ, Neuropathology and applied neurobiology, vol. 18(5), pp. 467–473, Oct. 1992.*
Whitaker, JM, Journal of Immunology, vol. 129(6), pp. 2729–2733, Dec. 1982.*
Hashim, GA et al, Journal of Neuroscience research, vol. 16(3), apges 467–478, Nov. 1986.*
Wucherpfennig, KW etal, J. Exp. Med. vol. 179, pp. 279–290, Jan. 1994.*
Chou, CH et al, J. Neurochemisty, vol. 30, pp. 745–750, Apr. 1978.*
Chou, YK et al, Journal of Neuroimmunology, vol. 49(1–2), pp. 45–50 (abstract only), Jan. 1994.*
Whitaker, JN et al, Journal of Neuroimmunology, vol. 51(1), pp. 53–60, Jun. 1994.*
Tisch, R eta I, Proc. Natl. Acad. Sci., vol. 91, pp. 437–438, Jan. 1994.*
Martin, R etal, Springer Semin. Immunopathol., vol. 18, pp. 1–24, 1996.*
The Merck Manual of Diagnosis and Therapy, Seventeenth Edition, Beers et al, pp. 1474–1775, 1999.*
Lodge, PA et al, Annals of Neurology, vol. 36(5), pp. 734–740, Nov. 1994.*
Xian et al, Journal of Neuroscience, vol. 41(5), pp. 620–627, (abstract only), Aug. 1995.*
Sun, D et al, European J. Immunol., vol. 25(6), pp. 1687–1692(abstract only), Jun. 1995.*
Roth, HG et al, J. Neuroscience Research, vol. 17(4), pp. 321–328,(abstract only), 1987.*
Staugaitis, SM et al, J Cell Biology, vol. 110(5) pp. 1719–1727, May 1990.*
Boylan, KB et al, American Journal of Human genetics, vol. 40(5), pp. 387–400 (abstract only), May 1987.*
Yamamoto, Y et al, Journal of Biological Chemistry, vol. 269(50), pp. 31725–31730 (abstract only), Dec. 1994.*
Javed, NH et al, Journal of Imunology, vol. 155(3), pp. 1599–1605 (abstract only) Sep. 1992.*
Loosmore et al, Injection and Immunity 54(11):3653–3662, 1990.*
Sun et al. Proc. Natl. Acad. Sci 93: 7196–7201, 1996.*
Moreland et al. The American Journal of the Medical Sciences 305(1):40–51, 1993.*
Shalaky et al. Clinical Immunology and Immunopathology 74(2): 127–134, 1995.*

* cited by examiner

1: WHOLE CELL EXTRACT.
2: SOLUBLE FRACTION
3: INSOLUBLE FRACTION

1: INS. FRACTION.
2: CELL'S PELLET.
3: CELL'S SUP.
4: PBS-WASH I.
5: PBS-WASH II.

M 1 2 3

M 1 2 3

M 1 2 3

M = MARKER
1 = WHOLE CELL EXTRACT OF E.COLI CELLS
2 = SOLUBLE FRACTION OF E.COLI CELLS
3 = INSOLUBLE FRACTION OF E.COLI CELLS

SEQUENCE LISTING

<160> NUMBER OF SEQ ID NOS: 17

<210> SEQ ID NO 1
<211> LENGTH: 81
<212> TYPE: DNA
<213> ORGANISM: Guinea pig

<400> SEQUENCE: 1
tatggtaggc tccctgcccc agaagtcgca gaggtctcaa gatgaaaacc cagtagtcca      60
cttcggtggc ggaggatcag a      81

<210> SEQ ID NO 2
<211> LENGTH: 81
<212> TYPE: DNA
<213> ORGANISM: Guinea pig

<400> SEQUENCE: 2

```
tatggtaggc tccctgcccc agaagtcgca gaggtctcaa gatgaaaacc cagtagtcca    60
cttcggtggc ggaggatcac a                                              81

<210> SEQ ID NO 3
<211> LENGTH: 66
<212> TYPE: DNA
<213> ORGANISM: Guinea pig

<400> SEQUENCE: 3
tatggctggc tccctgcccc agaagtcgca gaggtctcaa gatgaaaacc cagtagtcca    60
cttcga                                                               66

<210> SEQ ID NO 4
<211> LENGTH: 63
<212> TYPE: DNA
<213> ORGANISM: Guinea pig

<400> SEQUENCE: 4
tatggatgaa aatccagtag ttcattttttt taaaaatatt gtaacccac gtaccccacc   60 cga                                                                  63

<210> SEQ ID NO 5
<211> LENGTH: 27
<212> TYPE: DNA
<213> ORGANISM: Rat

<400> SEQUENCE: 5
agctcatatg gcatcacagg ggagacc                                        27

<210> SEQ ID NO 6
<211> LENGTH: 31
<212> TYPE: DNA
<213> ORGANISM: Rat

<400> SEQUENCE: 6
agctaagctt cgcgtcttgc tatgggagat c                                   31

<210> SEQ ID NO 7
<211> LENGTH: 66
<212> TYPE: DNA
<213> ORGANISM: Homo sapiens

<400> SEQUENCE: 7
tatgtttaaa ggggtagatg ctcaagggac cctttctaaa attttttaaat tgggaggtag   60 agatca                                                               66

<210> SEQ ID NO 8
<211> LENGTH: 66
<212> TYPE: DNA
<213> ORGANISM: Homo sapiens

<400> SEQUENCE: 8
tatgatctct acctcccaat ttaaaaattt tagaaagggt cccttgagca tctacccctt    60
taaaca                                                               66

<210> SEQ ID NO 9
<211> LENGTH: 63
<212> TYPE: DNA
<213> ORGANISM: Homo sapiens

<400> SEQUENCE: 9
```

-continued

```
tatggatgaa aatccagtag ttcattttt taaaaatatt gtaaccccac gtaccccacc    60
cca                                                                 63

<210> SEQ ID NO 10
<211> LENGTH: 63
<212> TYPE: DNA
<213> ORGANISM: Homo sapiens

<400> SEQUENCE: 10
tatggggtgg ggtacgtggg gttacaatat ttttaaaaaa atgaactact ggattttcat    60
cca                                                                 63

<210> SEQ ID NO 11
<211> LENGTH: 63
<212> TYPE: DNA
<213> ORGANISM: Homo sapiens

<400> SEQUENCE: 11
tatggatgaa aatccagtag ttcattttt taaaaatatt gtaaccccac gtaccccacc    60
cga                                                                 63

<210> SEQ ID NO 12
<211> LENGTH: 65
<212> TYPE: DNA
<213> ORGANISM: Homo sapiens

<400> SEQUENCE: 12
agcttcgggt ggggtacgtg gggttacaat attttaaaa aaatgaacta ctggattttc    60
atcca                                                               65

<210> SEQ ID NO 13
<211> LENGTH: 66
<212> TYPE: DNA
<213> ORGANISM: Homo sapiens

<400> SEQUENCE: 13
tatgtttaaa ggggtagatg ctcaagggac cctttctaaa attttttaaat tgggaggtag    60 agatga                                                              66

<210> SEQ ID NO 14
<211> LENGTH: 68
<212> TYPE: DNA
<213> ORGANISM: Homo sapiens

<400> SEQUENCE: 14
agcttcatct ctacctccca atttaaaaat tttagaaagg gtgccttgag catctacccc    60
tttaaaca                                                            68

<210> SEQ ID NO 15
<211> LENGTH: 19
<212> TYPE: PRT
<213> ORGANISM: Homo sapiens

<400> SEQUENCE: 15

Asn Glu Asn Pro Val Val His Phe Phe Lys Asn Ile Val Thr Pro Arg
 1               5                  10                  15

Thr Pro Pro
```

-continued

```
<210> SEQ ID NO 16
<211> LENGTH: 20
<212> TYPE: PRT
<213> ORGANISM: Homo sapiens
<220> FEATURE:

<400> SEQUENCE: 16

Phe Lys Gly Val Asp Ala Gln Gly Thr Leu Ser Lys Ile Phe Lys Leu
  1               5                  10                  15

Gly Gly Arg Asp
             20

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence:Synthetic

<400> SEQUENCE: 17

Gly Gly Gly Gly Ser
1               5
```

PSEUDOMONAS EXOTOXIN-MYELIN BASIC PROTEIN CHIMERIC PROTEINS

FIELD OF THE INVENTION

The present invention relates to antigen-toxin chimeric proteins useful in the targeted immunotherapy of autoimmune diseases, and particularly of multiple sclerosis.

BACKGROUND OF THE INVENTION

The development of selective immunosuppressive agents is one of the major goals in the treatment of autoimmune diseases. In the ignorance of the identity of the specific antigen involved, treatment has until now been oriented toward nonspecific killing of rapidly dividing cells by means of cytotoxic agents, as well as inhibiting the action of mediators of inflammation with anti inflammatory agents.

More recently, specific and selective agents for the therapy of disorders of the immune response have been developed, based on our increased understanding of the immune response, advances in genetic engineering and improved models of autoimmune diseases.

The well studied animal model Experimental Autoimmune Encephalomyelitis (EAE) is known to be induced by Myelin Basic Protein (MBP) or its immunogenic determinants, in many mammalian species when injected under appropriate conditions. MBP is a major component of central nervous system (CNS) myelin proteins. It has been proposed that MBP stimulates populations of T cells causing them to migrate into the central nervous system and initiate a response that results in perivascular cuffing lesions and demyelination characteristic of multiple sclerosis. This model can also be induced by injecting (MIBP-specific -T helper cells into murine animals.

Many approaches have been taken to inhibit the EAE model. Monoclonal antibodies specific to the MBP-1a complex were reported to inhibit EAE in H-$2^S$ mice (1–2)

Other approaches to the treatment of multiple sclerosis (MS) include the administration of synthetic T-cell receptor peptides (3), altered peptides of MBP (4), copolymer-1—a synthetic random copolymer of amino acids (U.S. Pat. No. 3,849,550) and various interferons (5).

A different approach to the treatment of autoimmune diseases relates to the use of chimeric cytotoxic molecules that are produced by gene fusion techniques. These molecules utilize portions of toxins such as Pseudomonas exotoxin (PE) while eliminating its nonspecific cell binding properties. Specificity is added to the truncated or modified toxin molecules by fusion of the toxin moiety with a recognition element which directs the chimeric protein to selected target cells expressing a specific receptor.

Effective chimeric cytotoxins have been constructed by fusion of cDNA's encoding IL2 IL4, IL6, TGFα, anti Tac and CD4 with PE (6–11).

One of the chimeric proteins, IL2-PE40 has been designed to target and selectively eliminate activated T cells expressing IL2 receptors. IL2-PE40 was found to be an effective and selective immunosuppressive agent for IL2 receptor targeted therapy in many models of disorders of the immune response, where activated T cells play a crucial role (12–19).

Using a highly purified preparation (20), IL2-PE40 has been shown to (a) delay and mitigate adjuvant induced arthritis in rats (21), (b) significantly prolong the survival of vascularized heart allografts in mice (22), (c) reduce the incidence and severity of experimental autoimmune uveoretinitis (EAU) in rats, (23), (d) suppress the growth of a T cell lymphoma in mice (24), (e) significantly reduce the clinical rejection score and cumulative rejection rate in orthotopic corneal grafts in rats (25) and (t) prevent the characteristic features of EAE in rats and mice (26–27).

Although cytokine-toxin chimeric proteins such as IL2-PE40 have been shown to be an effective and selective immunosuppressive agent, its effects are not limited to specific antigen activated cells but rather involve all IL2 receptor positive cells (12).

In contrast to many strategies undertaken or proposed today to treat EAE or MS patients, there remains a need for a specific approach that targets only the pathogenic cells and will leave other immune responses fully operative.

Oligonucleotides coding for an MBP encephalogenic moiety fused to a cDNA encoding a truncated or mutated full length PE gene were disclosed by Steinberger I., et al (Third International Conference on Neuro-immunology, Jerusalem, Israel (1991), Third International Symposium on Immuno-toxins Jerusalem (1992)). The DNA was expressed in *E. Coli* and the resulting chimeric proteins efficiently killed αMBP T cells while having no effect on non-target cells.

BRIEF SUMMARY OF THE INVENTION

It is an object of the present invention to provide a chimeric protein useful in the treatment of an autoimmune disease.

It is a further object of the present invention to provide a method of treatment of autoimmune diseases such as multiple sclerosis.

The present invention relates to the construction, characterization and purification of chimeric molecules comprising a myelin basic protein moiety linked to a toxin moiety that are efficient and selective novel agents to target and specifically kill αMBP specific T cells, as well as peripheral blood cells from MS patients. According to one aspect of the present invention, there is provided a chimeric protein comprising a *Pseudomonas aeruginosa* exotoxin (PE) moiety linked to a myelin basic protein (MBP) moiety selected from the group comprising: (a) MBP; (b) amino acids 69–88 of guinea-pig myelin basic protein or an antigenic portion thereof; (c) amino acids 84–102 of human myelin basic protein or an antigenic portion thereof; (d) amino acids 143–168 of human myelin basic protein or an antigenic portion thereof; and (e) an amino acid sequence in which one or more amino acids have been deleted, added, substituted or mutated in the amino acid sequences of (a), (b), (c) or (d), the modified sequence retaining at least 75% homology with the unmodified amino acid sequences.

Analysis of the Pseudomonas exotoxin has revealed that it is comprised of several functionally distinct domains, referred to as domains I (a and b), II and III. Preferably, the Pseudomonas toxin moiety comprises the full length exotoxin or is a mutated or truncated derivative of said exotoxin. The exotoxin may be derived from domains II and III of the exotoxin. Alternatively, the Pseudomonas toxin moiety may be derived from a Pseudomonas exotoxin mutated, for example, at one or more of positions 57, 246, 247, and 249. Such a mutated PE is referred to as PE66$^{4Glu}$.

In an alternative embodiment the invention relates to a chimeric protein comprising a full length myelin basic protein linked to an optionally mutated or truncated Pseudomonas exotoxin moiety.

In either embodiment of the invention the myelin basic protein moiety and toxin moiety may be linked directly or indirectly. If the two moieties are indirectly linked then they are preferably joined by means of a linker sequence. As used herein the term "linker sequence" relates to any amino acid sequence comprising from 1 to 5 amino acids that may be repeated from 1 to 3 times, i.e. the linker may comprise up to 15 amino acid residues consisting of a pentapeptide repeated three times. Preferably the linker sequence is a pentapeptide comprising gly-gly-gly-gly-ser (SEQ ID NO:17).

A further aspect of the present invention relates to plasmids containing a DNA sequence encoding a molecule of the present invention and expression vectors capable of expressing said molecules. Suitable plasmids comprise a promoter operatively linked to a DNA sequence encoding a molecule of the present invention. Any prokaryotic promoter may be used such as PL, Tac and the like, preferably a bacteriophage T7 promoter is used. The term "operatively linked" is used herein to mean that the promoter sequence and the sequence to be expressed under the control of said promoter are spatially positioned in respect of one another such as to permit the induction of expression by said promoter. Thus, the promoter and sequence to be expressed may be separated by means of a spacer sequence. Any suitable expression vector may be utilized, preferably, the vector used is *E.coli.*

Also included in the scope of the present invention are salts of the described chimeric proteins. The term "salts" includes both salts of carboxy groups as well as acid addition salts of amino groups of the protein molecule. Salts of the carboxy group may be formed by methods known in the art and include both inorganic salts such as sodium, calcium, ammonium, ferric or zinc salts and the like as well as salts with organic bases such as triethanolamine, arginine, lysine, piperidine, procaine and the like. Acid addition salts include, for example, salts with mineral acids such as for example, hydrochloric acid, sulfuric acid or salts with organic acids such as acetic acid or oxalic acid.

The invention further relates to pharmaceutical compositions comprising at least one chimeric protein as defined above together with a pharmaceutically acceptable inert carrier. Preferably, the composition further includes a lysosomotrophic agent such as ammonium chloride, monensin and the like.

The proteins of the present invention may be administered by methods known in the art for the administration of proteins for example, oral, intravenous, intraarticular, subcutaneous, intramuscular, intra-peritoneal, intra-nasal, intrathecal intra-dermal, trans-dermal, by inhalation or any other route including the enteral route.

The chimeric protein of the present invention may be prepared by methods familiar to those skilled in the art for example, by chemical synthetic methods or by biotechnological (genetic) methods. If the latter is used a construct of the DNA encoding the chimeric protein is inserted into plasmid. A suitable vector is the selected and transformed by such a plasmid. The vector can then be stimulated to produce the desired chimeric protein.

DESCRIPTION OF THE DRAWINGS

The present invention will be better understood from the following detailed description of preferred embodiments, taken in conjunction with the following drawings in which.

1–4=250; 500; 1000; 1500 ng respectively (total protein concentration) of the insoluble fraction-guanidine hydrochloride treated BPP-PE chimeric proteins;

4*=BPP-PE chimeric proteins (1500 ng, total protein concentration) in the presence of αPE antiserum;

5–7=50; 100; 500 ng respectively of highly- purified IL2-PE40.

Figure 4:
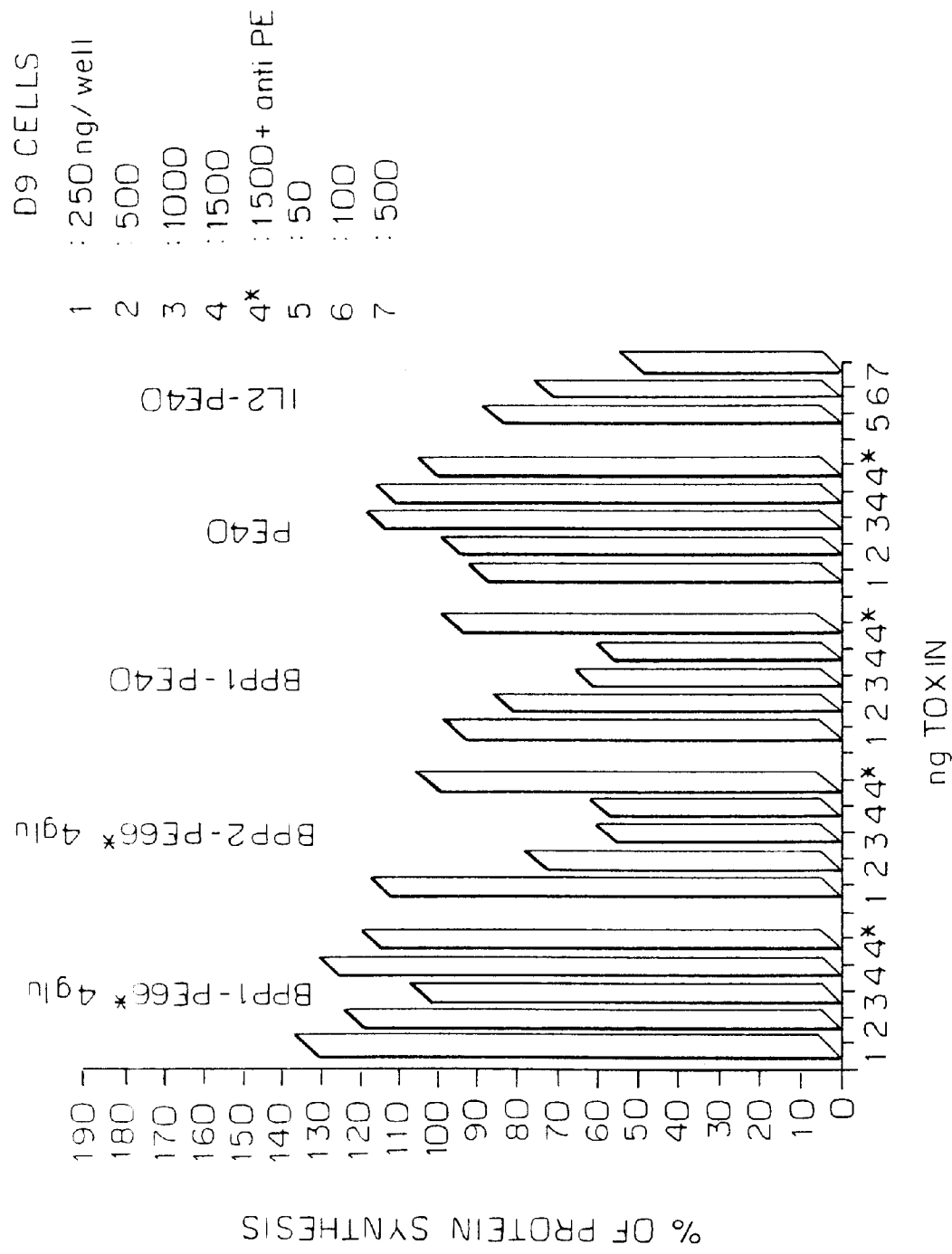
FIG. 4 illustrates cytotoxic activity of BPP-PE chimeric proteins on the αMBP T cell line-D9. BPP-PE chimeric proteins were added at the following various concentrations.
Figure 5:
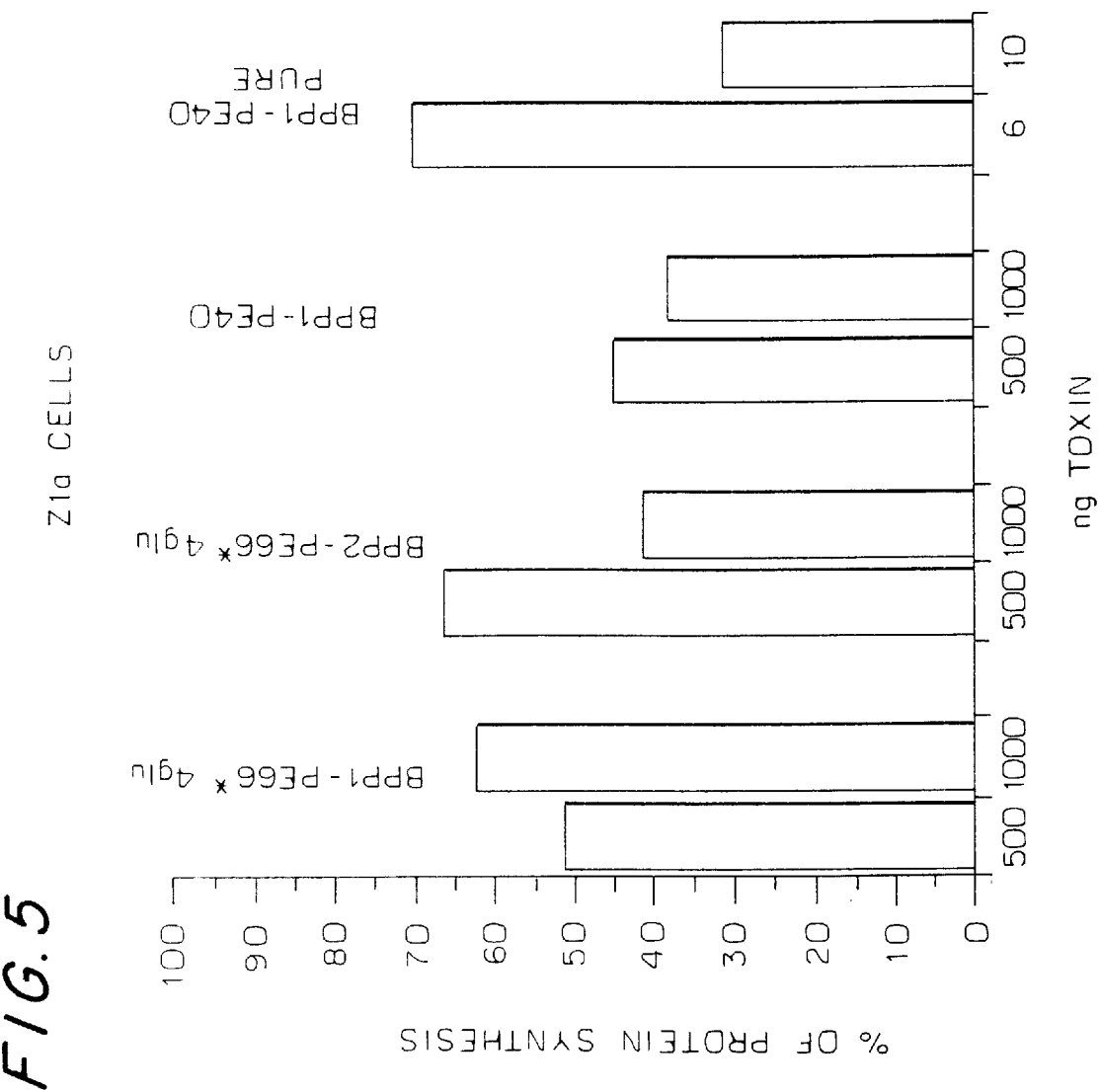
Figure 6:
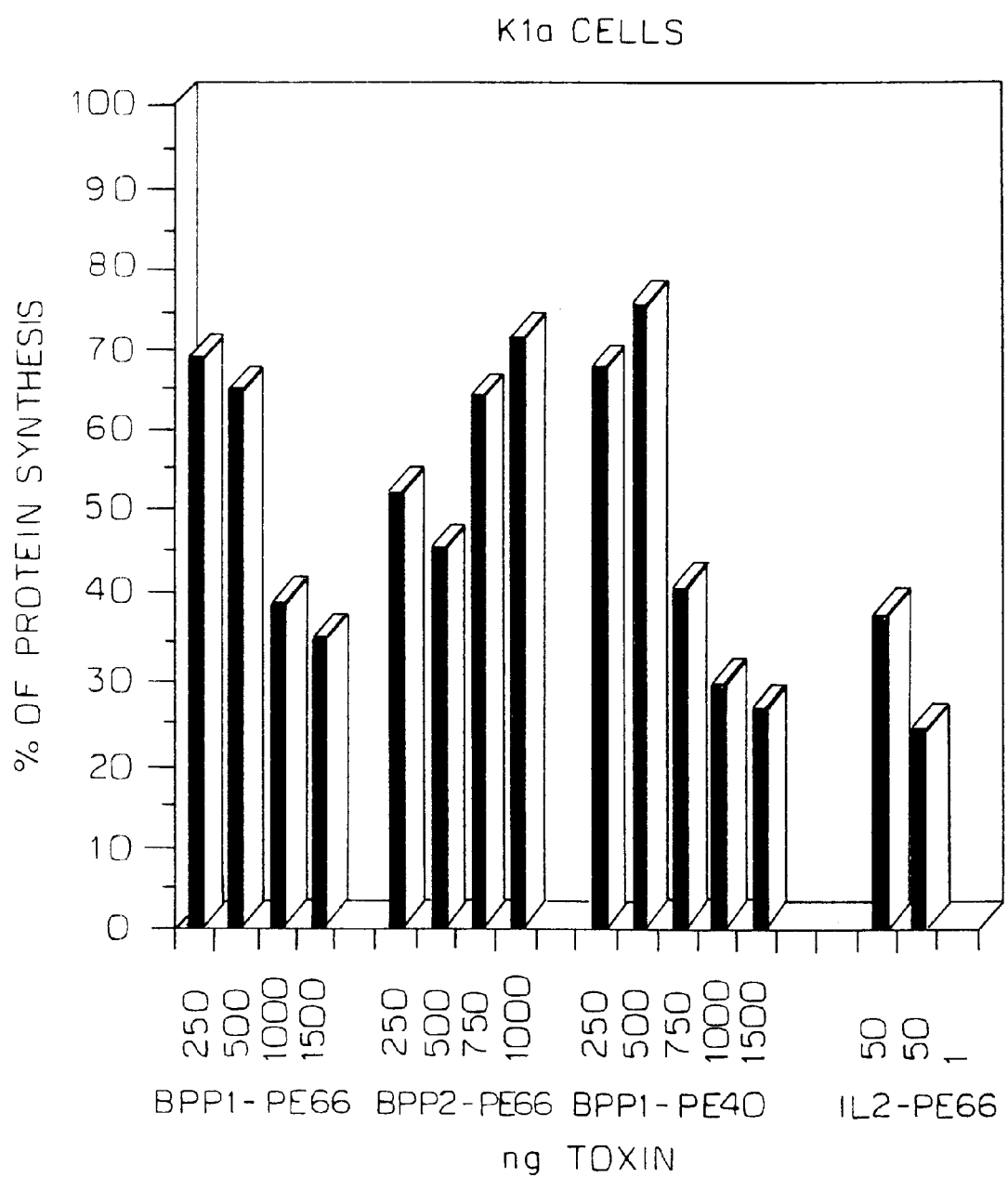
Figure 7:
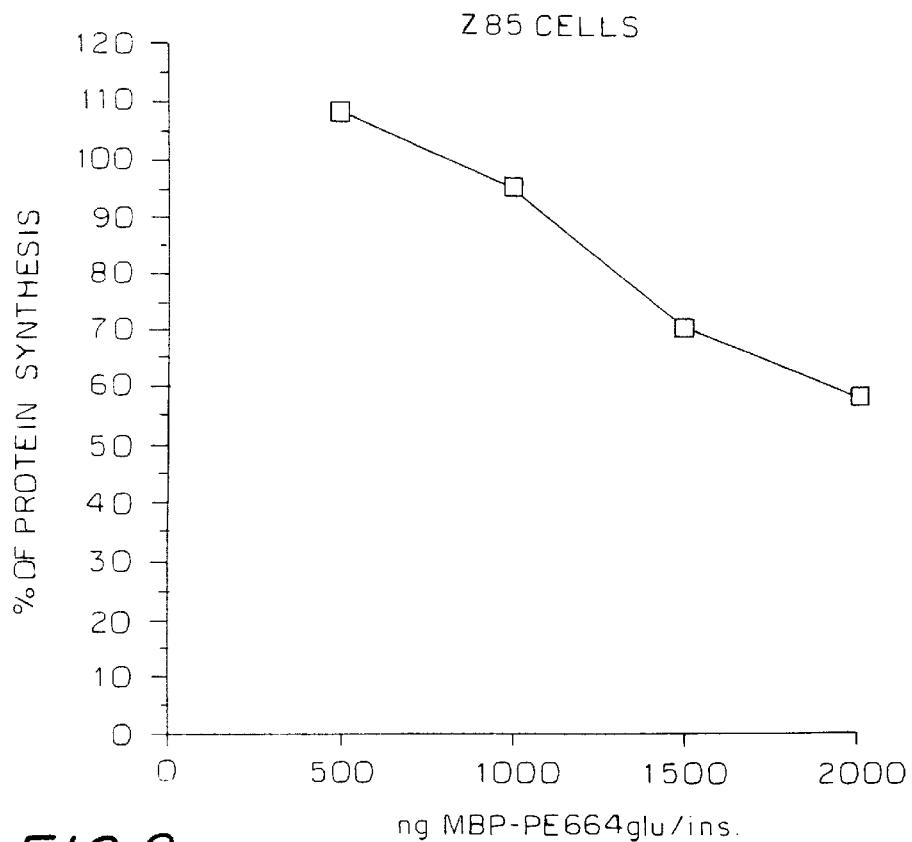
Figure 8:
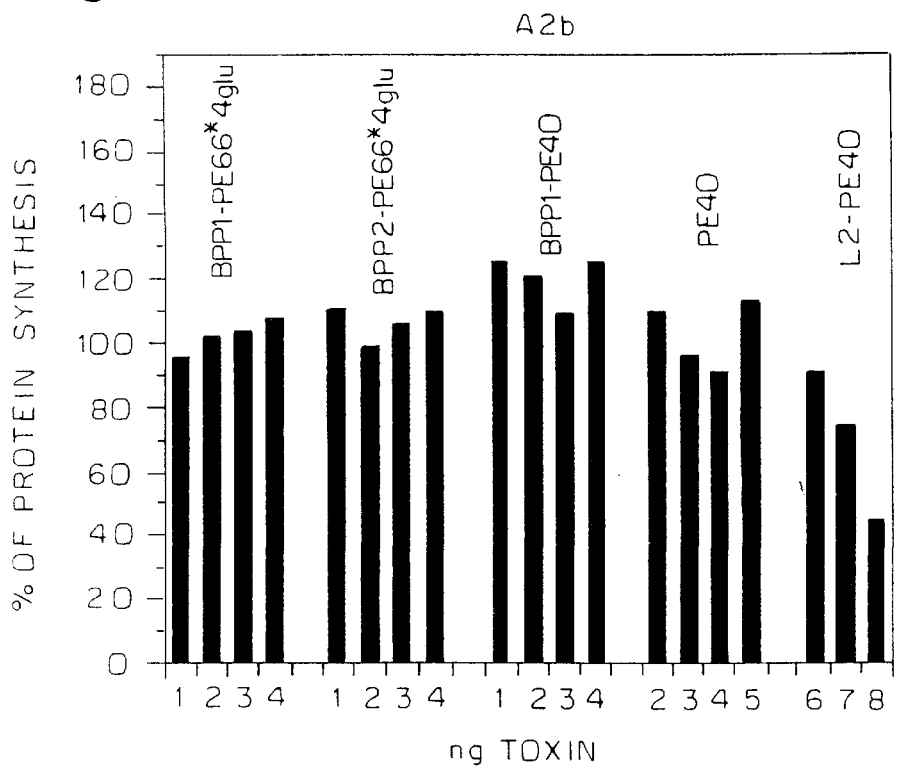

[$^3$H]-leucine incorporation into cellular proteins was measured. Results are expressed as percentage of control cells not exposed to BPP-PE chimeric proteins;

FIG. 5 illustrates cytotoxic activity of BPP-PE chimeric proteins toward the αMBP-T cell line Zla. Results are expressed as described in legend to FIG. 4;

FIG. 6 illustrates cytotoxic activity of BPP-PE chimeric proteins toward the αMBP-T cell line kla. Results are expressed as described in legend to FIG. 4;

FIG. 7 illustrates cytotoxic activity of MBP-PE66$^{4Glu}$ chimeric protein toward Z85 cells. Results are expressed as described in legend to FIG. 4;

FIG. 8 illustrates cytotoxic activity of BPP-PE chimeric proteins on the non-target T cell line-A2b. BPP-PE chimeric proteins were added at the following various concentrations:

1–5=250; 500; 1000; 1500 2000 ng respectively (total protein concentration) of the insoluble fraction-guanidine hydrochloride treated BPP-PE chimeric proteins;

6–8=50; 100; 500 ng respectively of highly purified IL2-PE40.

Figure 9:
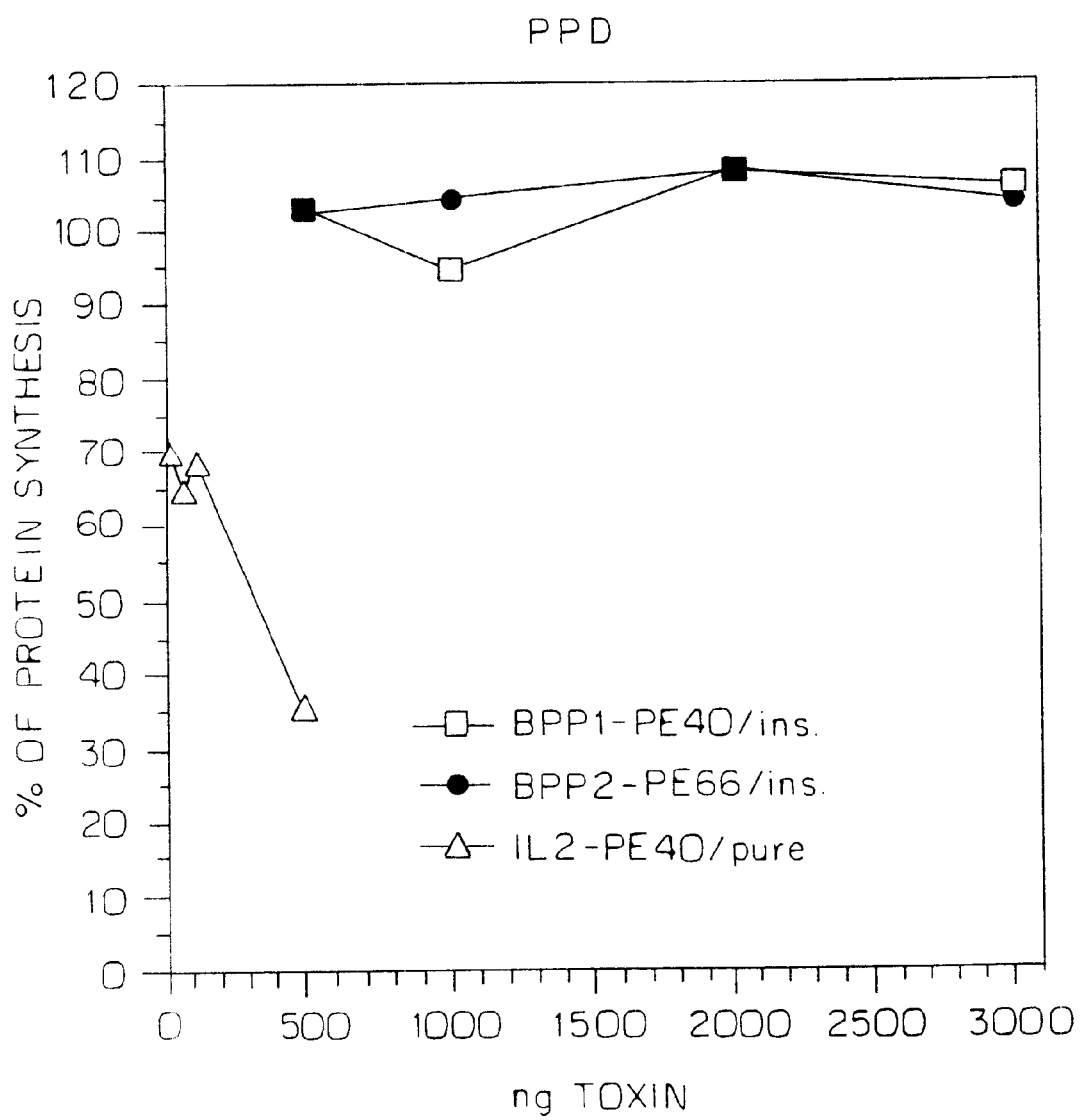
Figure 10:
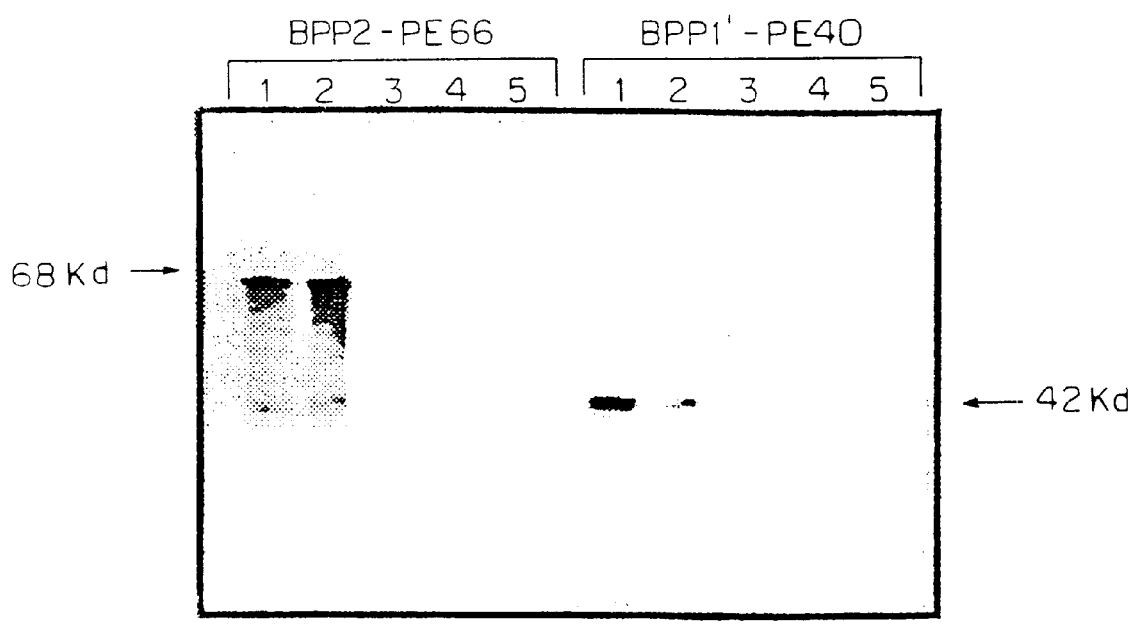

[$^3$H]-leucine incorporation into cellular proteins was measured. Results are expressed as percentage of control cells not exposed to BPP-PE chimeric proteins;

FIG. 9 illustrates cytotoxic activity of BPP-PE chimeric proteins toward the PPD-non target cells. Results are expressed as described in legend to FIG. 4:

FIG. 10 illustrates internalization of BPP2-PE66 and BPP1-PE40 chimeric proteins into PAS target cells. BPP2-PE66$^{4Glu}$ or BPP1'-PE40 (15 ug, total protein concentration of insoluble. fraction-guanidine hydrochloride treated) were added to the cells for 5 hr. Cells were washed and lysed and samples were applied for immunoblot analysis using anti PE antiserum.

Lane 1: BPP2-PE66$^{4Glu}$/BPP1'-PE40 respectively (3 ug, total protein concentration);

Lane 2: Insoluble fraction of lysed cells incubated with either of the BPP-PE chimeric proteins;

Lane 3: Soluble fraction of lysed cells incubated with BPP-PEs;

Lanes 4,5: Samples of the washing steps 1 and 4, respectively.

Figure 11:
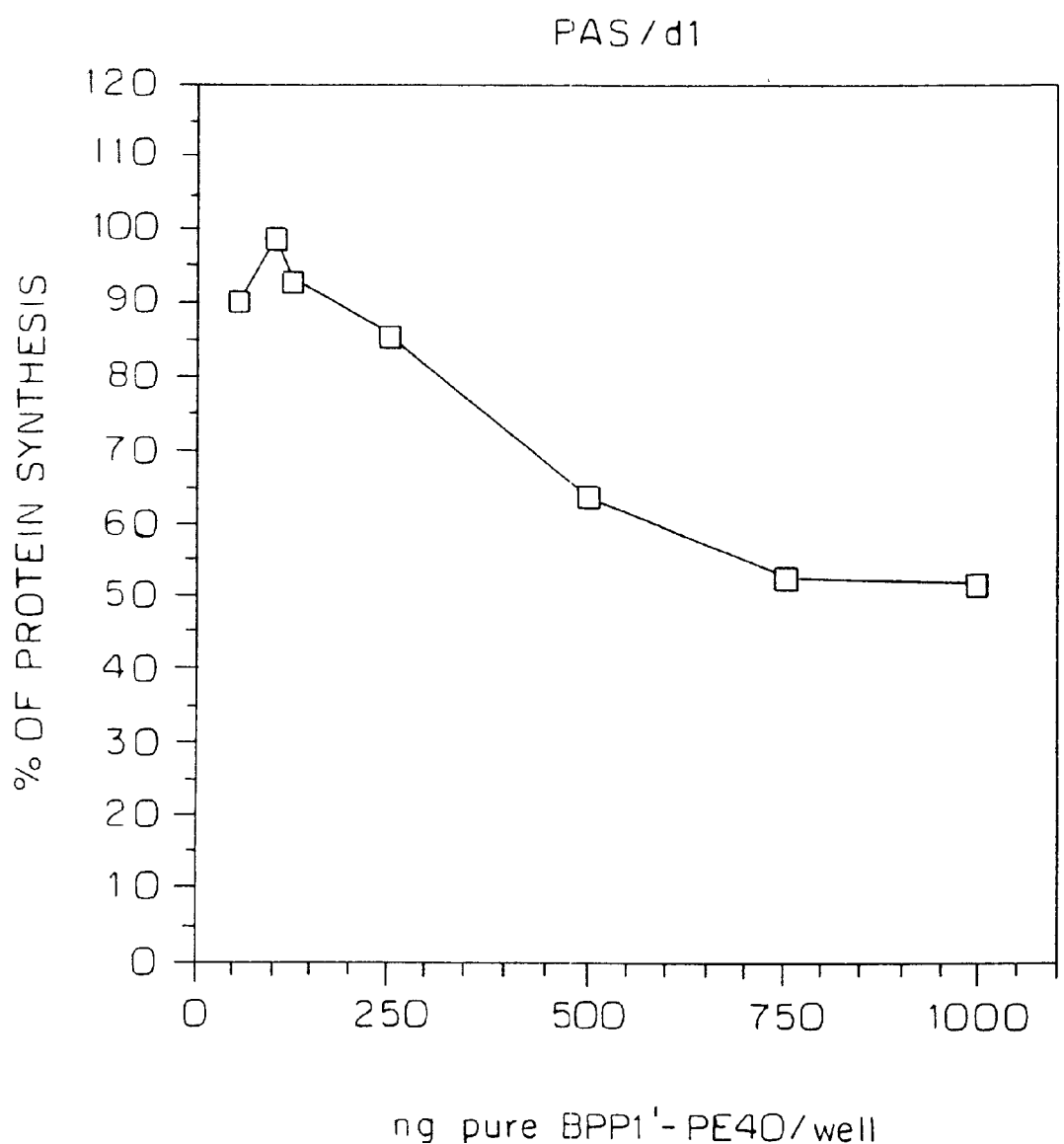
Figure 12:
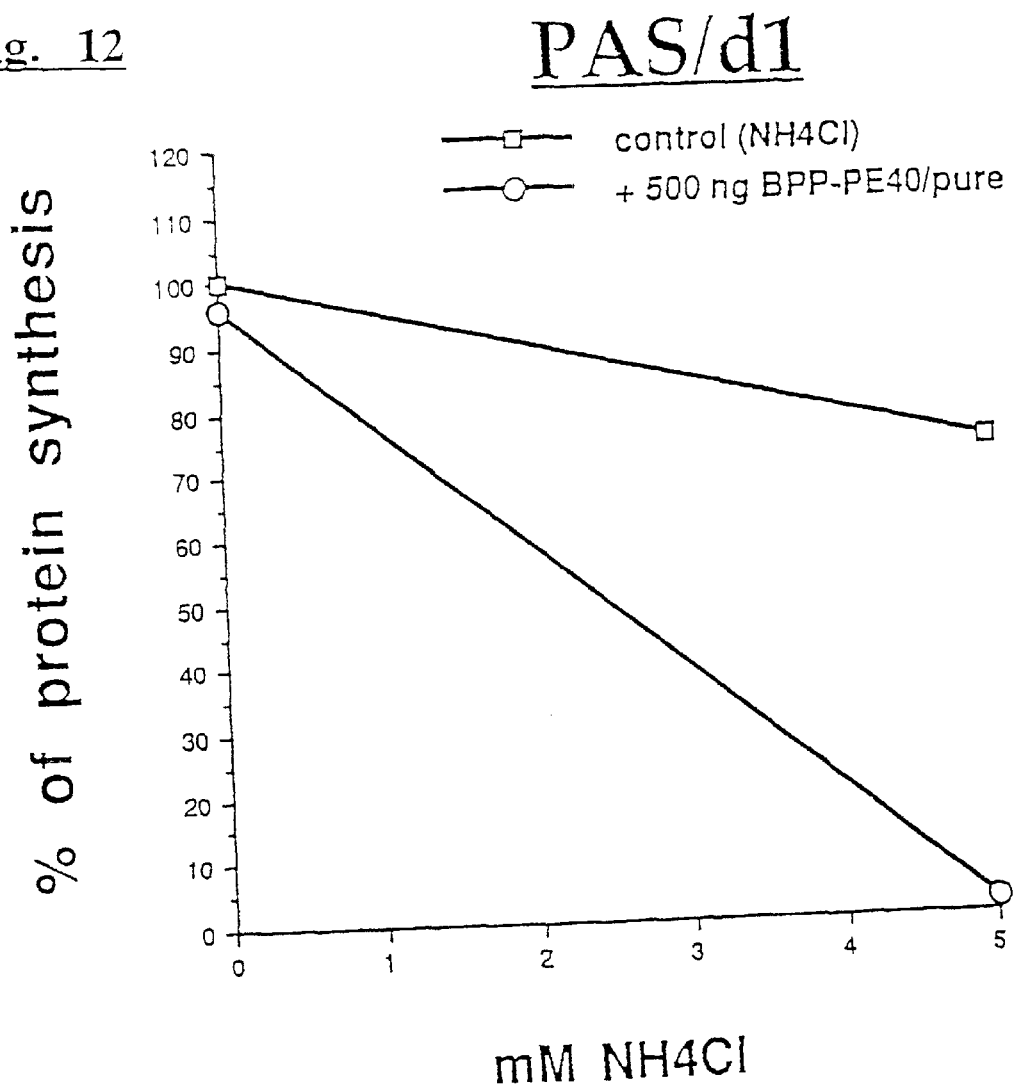
Figure 13:
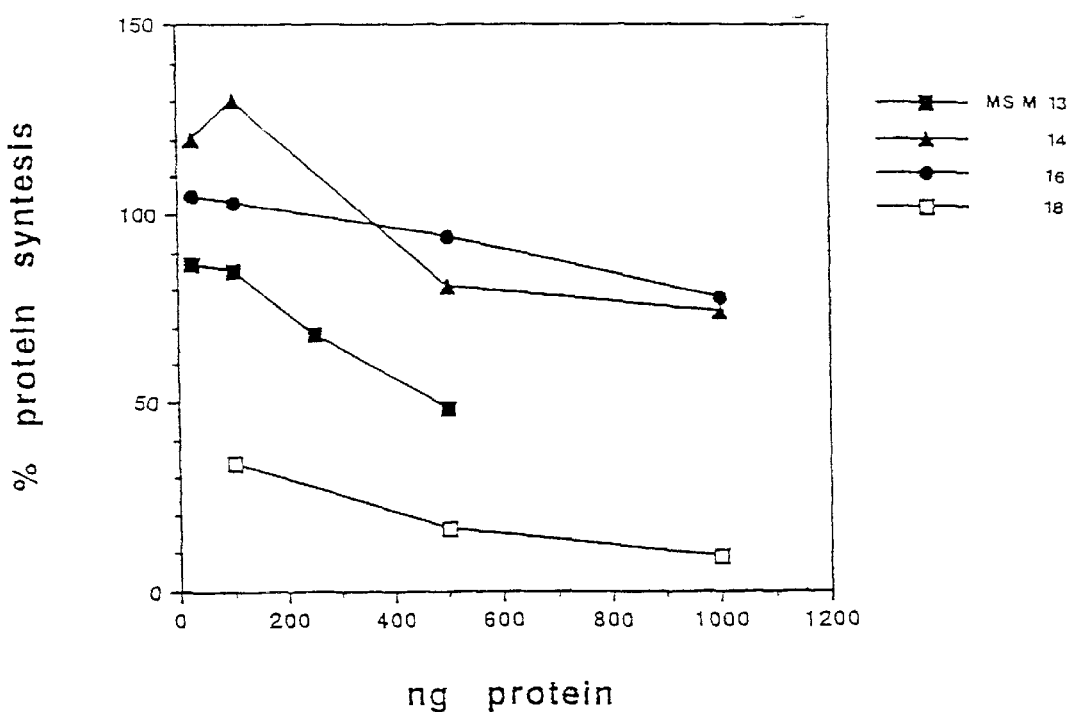
Figure 14A:
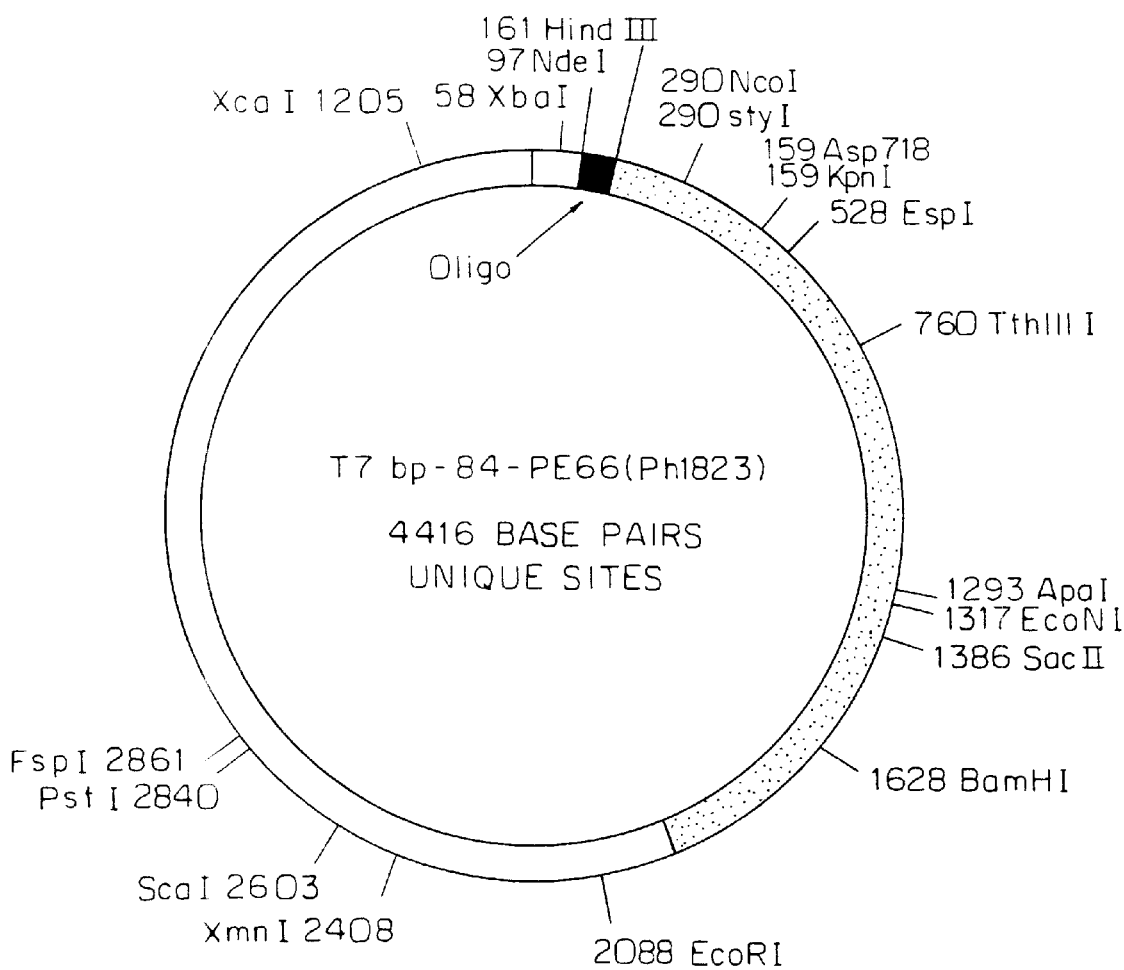
Figure 14B:
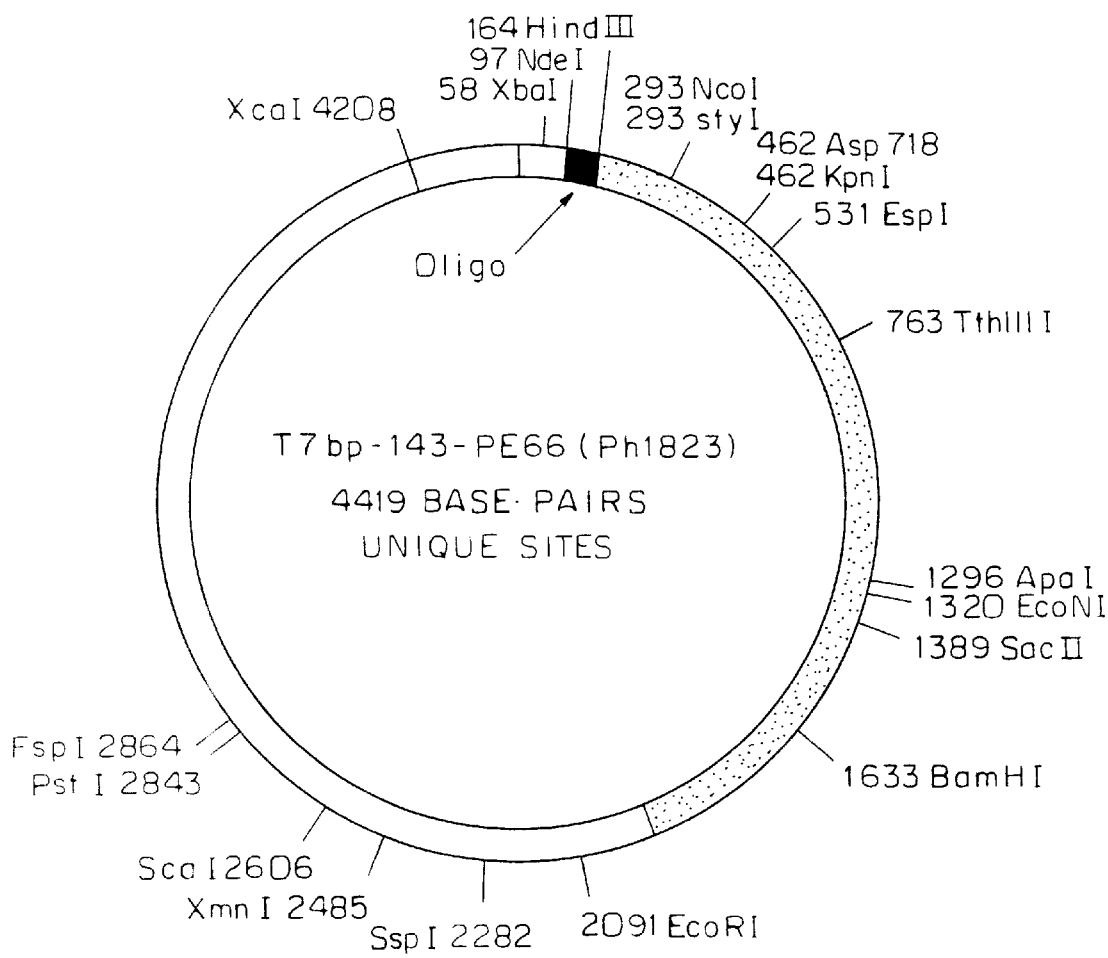
Figure 14C:
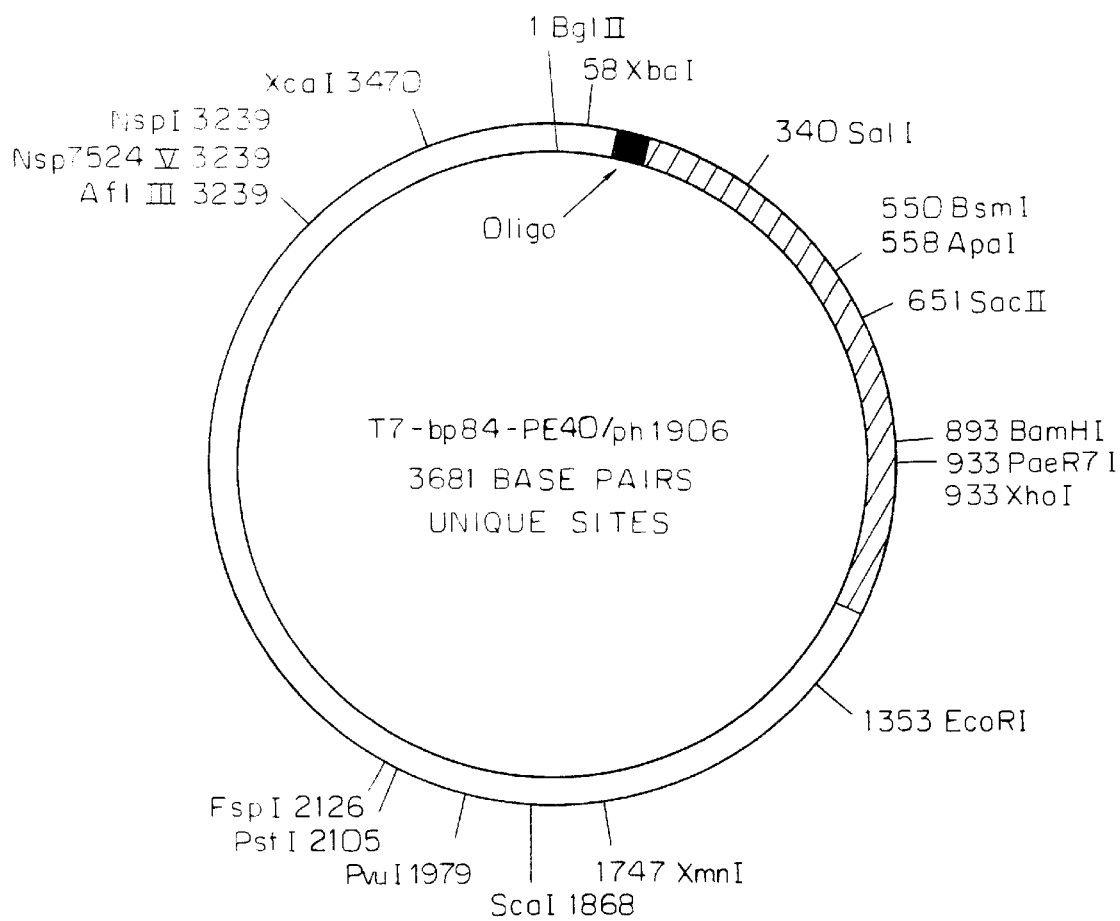
Figure 14D:
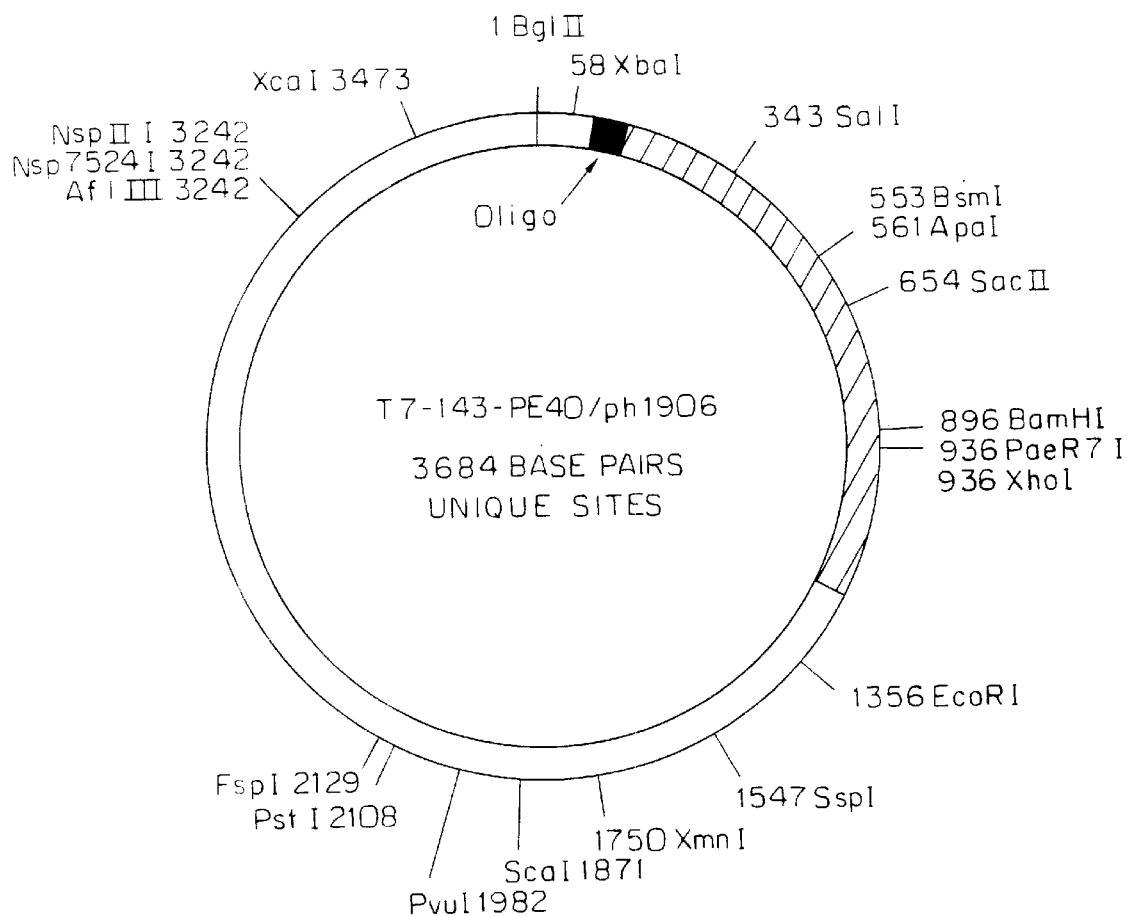
Figure 15A:
Figure 15B:
Figure 15C:

FIG. 11 illustrates cytotoxic activity of BPP1'-PE40 on PAS cells (αMBP T cells). Purified BPP1'-PE40 (-□-) was added at various concentrations to PAS cells at day 1 of the propagation period. Results are expressed as described in FIG. 4;

FIG. 12 illustrates the effect of $NH_4Cl$ on the cytotoxic activity of BPP1'-PE40 toward αMBP T cells. BPP1'-PE40 was added at a constant amount of 500 ng. Inhibition of protein synthesis by BPP1'-PE40 was measured in the presence of increasing concentrations of $NH_4Cl$ (-□-). The effect of $NH_4Cl$ alone at the different concentrations was also measured (-□-). Results are expressed as in FIG. 4;

FIG. 13 illustrates the effect of BPP1'-PE40 on PBL from MS patients. BPP1'-PE40 was added at various concentrations to PBL cells separated from the following MS patients: MSM 13 (-■-), MSM 14 (-Δ-), MSM 16 (-●-) and MSM 18 (-□-), Inhibition of protein synthesis was measured as described in FIG. 4;

FIGS. 14a–d are schematic representations of plasmids encoding human chimeric proteins; and FIGS. 15a–c illustrate SDS-PAGE profiles of E. coli cell fractions expressing human BPP-PE chimeric proteins: a) $BPP_{84-102}$-$PE66^{4Glu}$; b) $BPP_{143-168}$-$PE66^{4Glu}$; c) $BPP_{84-102}$-PE40.

DETAILED DESCRIPTION OF PREFERRED EMBODIMENTS

A. Construction of BPP-PE/MBP-PE Fusion Genes

Five peptide-toxin chimeric proteins were constructed. Three contained the BPP sequence coding for 19 amino acids (amino acids 69–88) of guinea pig-Myelin Basic Protein (29a). Three oligonucleotides each containing this guinea pig sequence were synthesized (oligos 1, 1' and 2, Table 1) and were each fused to the 5' end of a DNA fragment encoding a truncated form of PE (PE40) or a mutated full length PE sequence ($PE66^{4Glu}$). The BPP encoding sequences were preceded by a sequence encoding 2 amino acids Met-Val, in the cases of BPP1-$PE66^{4Glu}$ and BPP1'-PE40, and by a sequence encoding Met-Ala in the case of BPP2-$PE66^{4Glu}$.

The BPP/MBP encoding sequences were fused either directly to the mutated PE sequence (chimeric protein BPP2-$PE66^{4Glu}$) or via a linker sequence of 5 amino acids (gly-gly-gly-gly-ser) that was inserted between the BPP sequence and $PE66^{4Glu}$ (Table 1, oligo 1 chimeric protein BPP1-$PE66^{4Glu}$) or PE40 (Table 1 oligo 1', chimeric protein BPP1'-PE40).

In the fourth plasmid, pIS-3, a rat MBP sequence (30) was directly ligated to the $PE66^{4Glu}$ sequence (FIG. 1) whereas in the fifth pSM-8466 the sequence encoding for amino acids 84–102 of human MBP was ligated directly to the $PE66^{4Glu}$ sequence.

Summary of Plasmids and Their Contents (Construct (Plasmid Name))

1. BPP1-$PE66^{4Glu}$ (pIS-1)—69–88 guinea pig MBP & mutated PE, with linker
2. BPP1'-PE40 (pHL15)—69–88 guinea pig MBP & truncated PE, with linker
3. BPP2-$PE66^{4Glu}$ (pIS-2)—69–88 guinea pig MBP & mutated PE, no linker
4. MBP-$PE66^{4Glu}$-(pIS 3)—rat MBP & mutated PE, no linker
5. BPP84-$PE66^{4Glu}$ (pSM-8466)—84–102 human MBP & mutated PE, no linker.

TABLE I

Oligo's used for the synthesis of BPP-PE chimeric proteins

```
Oligo 1:
5' TATGGTAGGCTCCCTGCCCCAGAAGTCGCAGAGGTCTCAAGAT
GAAAACCCA GTAGTCCACTTCGGTGGCGGAGGATCAGA 3'
(SEQ ID NO: 1)
Oligo 1'
5' TATGGTAGGCTCCCTGCCCCAGAAGTCGCAGAGGTCTCAAGAT
GAAAACCCA GTAGTCCACTTCGGTGGCGGAGGATCACA 3'
(SEQ ID NO: 2)
Oligo 2
5' TATGGCTGGCTCCCTGCCCCAGAAGTCGCAGAGGTCTCAAGAT
GAAAACCCAGTAGTCCACTTCGA 3'
(SEQ ID NO: 3)
Oligo 3:
5' TATGGATGAAAATCCAGTAGTTCATTTTTTTAAAAATATTGTAA
CCCCACGTACCCCACCCGA 3'
(SEQ ID NO: 4)
```

PCR-primers for cDNA Encoding the Rat MBP in pMBP-1 Plasmid

IS 1: sense:
    5'AGC TCATATGGCATCACAGGGGAGACC3'
    (SEQ ID NO:5)

IS2: antisense:
    5'AGCTAAGCTTCGCGTCTTGCTATGGGAGATC 3' (SEQ ID NO:6)

A.1: Plasmids pIS-1, pIS-2 and pSM-8466

Figure 1:
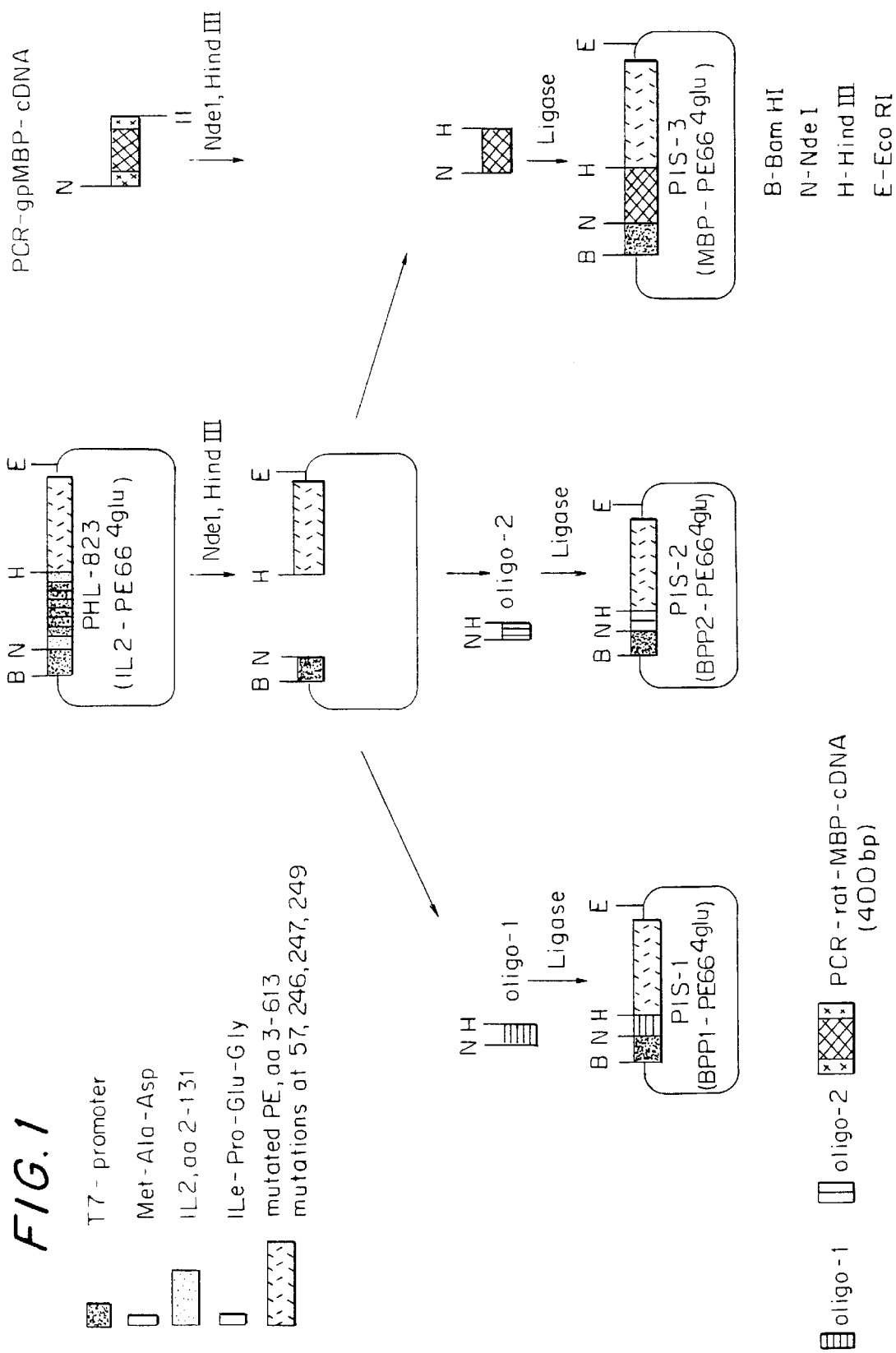
FIG. 1 is a scheme for the construction of expression plasmids pIS-1, pIS-2 and pIS-3 which encode the BPP1-PE66$^{4Glu}$, BPP2-PE66$^{4Glu}$ and MBP-PE66$^{4Glu}$, respectively, in which: B, Bam HI; H, Hind III; N, NdeI; and E, EcoRI.
Figure 2:
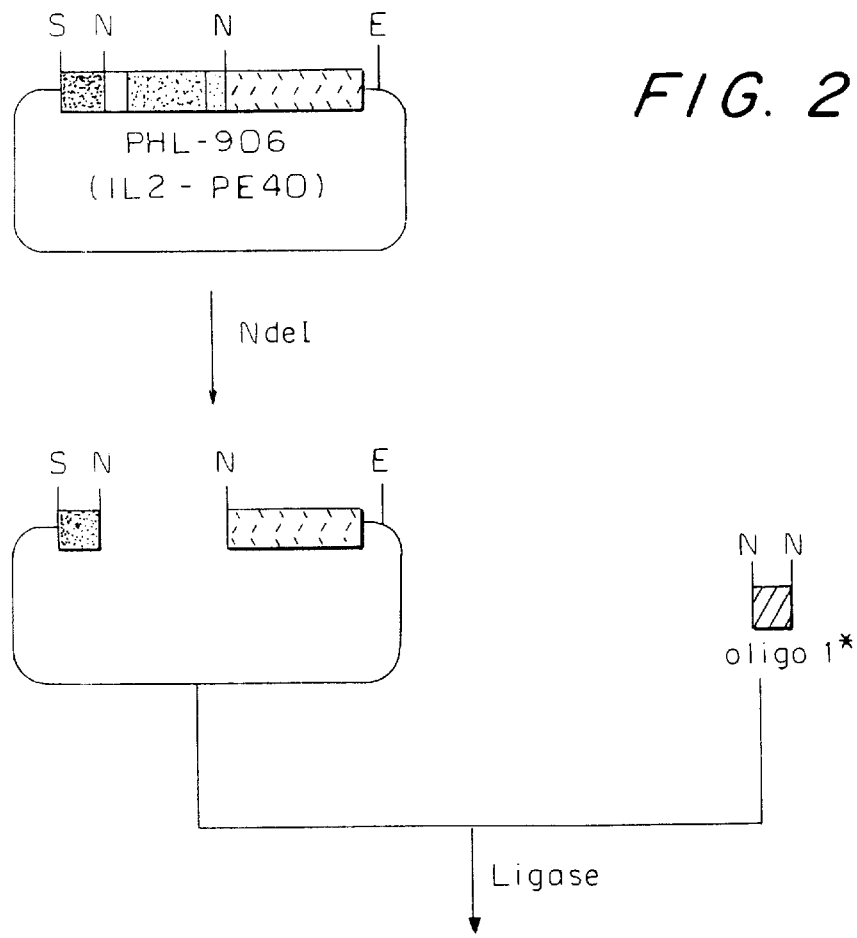
FIG. 2 is a scheme for the construction of expression plasmid pHL15, in which: B, Bam HI; N, NdeI; and E, EcoRI.
Figure 3A:
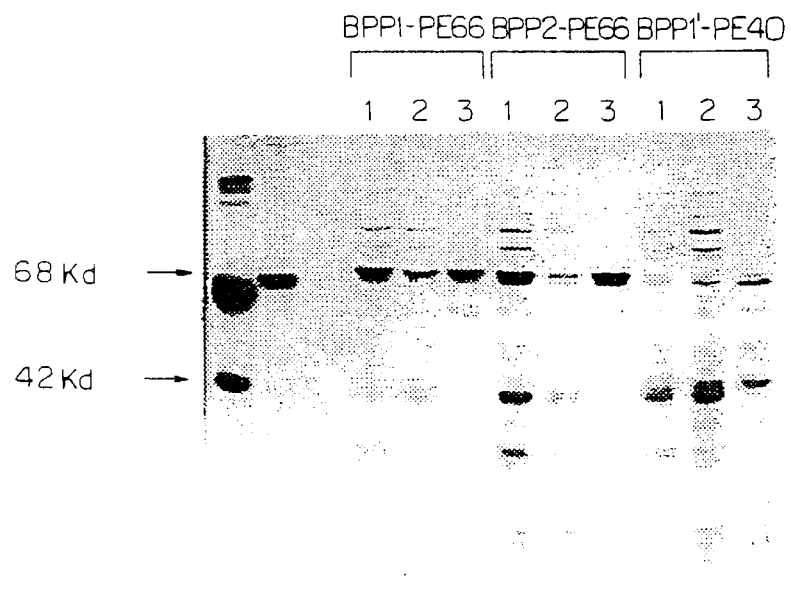
FIG. 3A illustrates a Coomassie blue stained gel showing SDS-PAGE analysis of bacteria cell fractions containing the BPP-PE chimeric proteins.
Figure 3B:
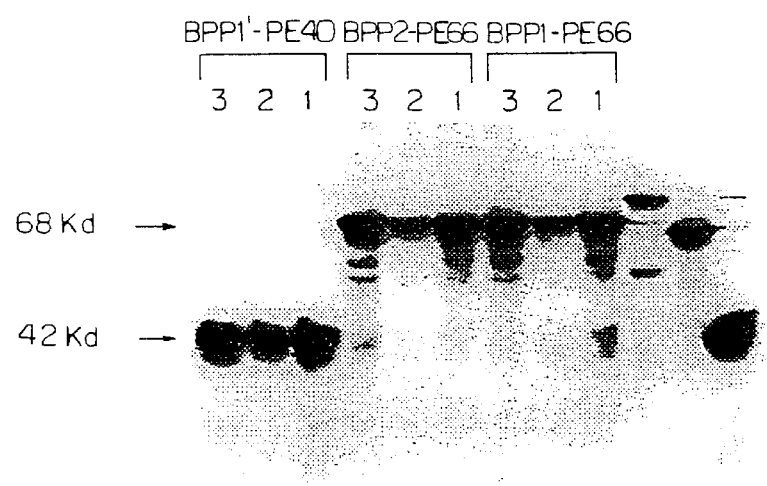
FIG. 3B illustrates immunobloting with anti PE antibodies and SDS-PAGE analysis of bacterial cell fractions containing the BPP-PE chimeric proteins.

Plasmids for the expression of the chimeric proteins under the bacteriophage T7 promoter were constructed as shown in FIGS. 1 and 2. Plasmids pIS-1, pIS-2 and pSM-8466 encoding BPP1-$PE66^{4Glu}$, BPP2-$PE66^{4Glu}$ and BBP84$PE66^{4Glu}$, respectively, were constructed from pHL823 (28) cut with NdeI and HindIII. The largest vector fragment (4.4 Kb) was ligated to either of three different synthetic oligonucleotides (oligo 1, 2 or 3, Table I and FIG. 1). The resulting plasmids were examined for size and for the expression of the encoded chimeric proteins in BL 21(λDE3) cells, see section G.

A.2: Plasmid pHL15 Which Encodes BPP1'-PE40

Plasmid pHL15 was constructed from pHL906 (29b) cut with NdeI. The largest vector fragment (4 kb) was ligated to a synthetic oligonucleotide (oligo 1', Table 1 and FIG. 2). Plasmid pHL15 was examined as described above.

A.3: Plasmid pIS-3 Which Encodes MBP-$PE66^{4Glu}$

Plasmid pIS-3, was constructed by fusing a 400 bp-PCR fragment corresponding to the whole rat MBP, to the larger fragment (4.4 Kb) of pHL823 cut with NdeI and Hind lll (FIG. 1). The PCR fragment was synthesized using, IS1 and IS2 primers (Table 1) and plasmid pMBP-1, kindly provided by L. Hood, California Inst. of Tech, USA. The PCR product was cut with NdeI and Hind lll and ligated to pHL823 cut with the same enzymes. Plasmid pMBP-1 contains the full size cDNA for rat MBP.

The sequences of the chimeric genes constructed were confirmed by DNA sequence analysis (data not shown).

B. Protein Expression

The plasmids encoding the fusion genes were transformed into E.coli strain BL-21 DE3 using the heat shock protocol (32). The transformed E.coli colonies were grown and selected from Ampicillin (100 (g/ml) agar plates. Selected colonies were further grown in SLB medium containing Ampicillin (50 (g/ml) until OD650 reached 0.5. Induction was then performed for 90 minutes using iso-propyl-(-D-galactoside (IPTG) (1 mM final concentration).

A pellet of expressed cells was suspended in TE buffer (50 mM Tris pH 8.0, 1 mM EDTA) sonicated (six 30-sec bursts, at 100 W) and centrifuged at 10,000×g for 15 min. The supernatant (soluble fraction) was removed and kept for analysis. The pellet was denatured in 4 vol (v/w) of extraction buffer (7M Gu-HCl, 0.1M Tris pH 8.0, 1 mM EDTA, 1 mM DTT) and sonicated (six 30-sec bursts 100 W). The suspension was stirred for 1 hr at 4° C. The suspension was cleared by centrifugation at 12,000 g for 15 min and the pellet discarded. The clear supernatant was then diluted 4-fold with phosphate buffer saline (PBS) and dialyzed against PBS. The dialyzed material was centrifuged at 12,000 g for 10 min.

The resulting supernatant (insoluble fraction, guanidine hydrochloride treated) was used as a source of the chimeric proteins for most experiments.

C. Characterization and Subcellular Localization of the BPP-PE Chimeric Proteins The new expressed chimeric proteins were characterized by SDS polyacrylamide gel electrophoresis (PAGE). These proteins migrated with an apparent molecular mass of approximately 42.9 Kd and 68.3–68.9 Kd, corresponding to the expected molecular mass of BPP1'-PE40, BPP1-$PE66^{4Glu}$/BPP2-$PE66^{4Glu}$/BPP84-$PE66^{4Glu}$, respectively (FIG. 3A). The molecular weight of MBP-$PE66^{4Glu}$ is 80 Kd. Immunoblots showed that the chimeric proteins react with the polyclonal anti-PE antiserum (FIG. 3B).

Extracts from the cells displayed ADP-ribosylation activity (31) as shown in Table II below. To identify the subcellular localization of the expressed chimeric proteins subcellular fractionation was performed. Each subfraction was tested for its ADP ribosylation activity using wheat germ extracts enriched in Elongation Factor 2. According to the enzymatic activity the three different chimeric proteins (BPP1-$PE66^{4Glu}$, BPP2-$PE66^{4Glu}$ and BPP1'-PE40) are expressed and distributed similarly in the different subfractions.

About 60–70% of the total activity was found associated within the soluble fraction and only 30–40% within the insoluble fraction. However, the insoluble fraction was found to be the most enriched one for the proteins, showing 7 to 16-fold higher values (specific activity) than those calculated for the soluble fraction (Table II). Thus BPP-PE chimeric proteins were purified from the insoluble fraction (see below). It should be noted that only basal levels of BPP-PE proteins were found in the periplasm fraction or in the incubation media.

TABLE II

| | BPP1-$PE66^{4Glu}$ | | BPP2-$PE66^{4Glu}$ | | BPP1'-PE40 | |
|---|---|---|---|---|---|---|
| SAMPLE | % activity | sp. activity | % activity | sp. activity | % activity | sp. activity |
| Soluble fraction | 68 | 0.9 | 60 | 0.7 | 67 | 0.6 |
| Insoluble fraction | 32 | 6.3 | 40 | 11.2 | 33 | 6.4 |

D. Cytotoxic Activity of BPP-PE Chimeric Proteins

The cytotoxic activity of the different BPP-PE chimeric proteins was tested on MBP-specific encephalitogenic T cell lines. The cell lines ((MBP—specific T cell lines: Z1a, D9, PAS, K1a and control cell lines: A2b. PPD, available from the inventors) were maintained in culture by alternating specific antigen stimulation for 3 days and propagation phases for another 5–7 days. Stimulation of MBP specific encephalitogenic MBP-T line cells (3×105 cells/ml) was done in the presence of 15 μg/ml guinea-pig MBP for two to three days with $15\times10^6$ cells/ml syngeneic irradiated thymocytes as antigen presenting cells (APC) in RPMI-1640 supplemented with 1% syngeneic rat serum, 2 mM-L glutamine, 1 mM sodium pyruvate, $5\times10^{-5}$ M β-mercaptoethanol, 100 μg/ml penicillin and 100 μg/ml streptomycin. The activated lymphoblasts were separated from the thymocytes and debris by centrifugation over a Ficoll paque gradient (Pharmacia). The blasts are found in the interface. Blasts were then expanded in the same medium minus antigen and rat serum, enriched with 10% heat inactivated fetal calf serum (FCS) and 10% ConA activated spleenocyte supernatant (conditioned medium which contains TGCF) or 25 units/ml of human rIL2.

Assays were performed using the insoluble fraction of the different chimeric proteins, diluted in PBS containing 0.2% bovine serum albumin (BSA). They were then added at various concentrations to the (MBP-T cells in a 96-well plate ($2–4\times10^4$ cells/well) in triplicate at the third day (d3) of the propagation phase. The cells were incubated in 5% $CO_2$, in air at 37° C. for 18–24 hr, with the addition of 2 μci of [3H]-leucine or 1 μci of [3H]-thymidine for an additional 12–16 hr. Cells were then harvested and incorporated radioactivity was measured. When assays were performed on HUT102 control cells, the radioactive material was added for only 4 hr. before harvesting the cells. Percentage of protein synthesis inhibition was calculated from control cells not exposed to any chimeric proteins.

As shown in FIGS. 4–6 specific αMBP T cell lines (D9, Z1a and K1a respectively) were sensitive to the cytotoxic activity of these BPP-PE chimeric proteins demonstrating a 60–70% inhibition of protein synthesis at the highest concentration tested. Protein synthesis inhibition was concentration dependent.

Chimeric protein BPP1-$PE66^{4Glu}$ was not cytotoxic to D9 target cells in contrast to the other two chimeras (BPP2-$PE66^{4Glu}$ and BPP1'-PE40) (FIG. 4). When the cytotoxic effect of BPP-PE chimeric proteins was tested on DNA synthesis, similar results were observed (results not shown) demonstrating that the chimeric proteins irreversibly inhibit protein synthesis thus causing cell death. As the insoluble fraction of expressed cells was used in most of these experiments, we used the insoluble fraction of cells expressing only the toxin moiety of the chimeric protein, (PE40), as a control to test for non-specific activity associated with the insoluble fraction preparations.

The insoluble fraction of PE40 had no cytotoxic effect on target (FIG. 4) or non target cells. The insoluble (ins.) fraction of MBP-$PE66^{4Glu}$ was cytotoxic to Z85 cells. At the highest concentration tested (2,000 ng) an inhibition of 58% of protein synthesis was observed (FIG. 7).

De novo expression of interleukin 2 receptor molecules (IL2R) appears during the activation process of a T cell line induced by an antigen, thus we tested the cytotoxic activity of IL2-PE chimeric proteins on the different antigen specific T cell lines as positive controls. Highly purified IL2-$PE66^{4Glu}$ caused 40–75% inhibition of protein synthesis in the different αMBP T cell lines tested (FIGS. 4–6).

E. Specificity of Activity of BPP/MBP-PE Chimeric Proteins

After demonstrating that BPP-PE chimeric proteins had a cytotoxic effect on αMBP T cell lines, we assessed the specificity of the response to the chimeric proteins. As shown in FIG. 4, the cytotoxic effect of BPP-PE chimeric proteins on the αMBP T cell line D9 was completely blocked by excess of polyclonal αPE, demonstrating the specificity of their action.

The effect of BPP-PE proteins was also tested on the non target cell lines A2b or PPD. The A2b cell line which is specific to mycobacterial antigen, cross reactive with rat cartilage and it is involved in mediating adjuvant arthritis. The PPD cell line is specific to Purified Protein Derivative of Mycobacterium tuberculosis. Both T cells were maintained in culture in the same conditions as that of αMBP T cells.

As shown in FIGS. 8 and 9, A2b or PPD control cell lines were unaffected by the action of the BPP-PE chimeric proteins, showing that the effect is a highly specific response. The activity of BPP-PE chimeric proteins was also tested on other non target cells-HUT 102 cells, a human HTLV-I T cell leukemia cell line which expresses the high and the low affinity forms of IL2R. This cells were maintained in RPMI 1640 supplemented with 10% FCS. HUT 102 was a gift of T. A. Waldmann (National Cancer Institutes). No cytotoxic effect was observed by the BPP-PE chimeric.

F. Internalization of Chimeric Proteins Into Target Cells

As another approach to confirm internalization of BPP-PE chimeric proteins into target cells we followed the existence of the proteins following incubation, within the cells, by immunoblot analysis.

Internalization of chimeric proteins into target cells was assayed by incubating chimeric proteins BPP2-PE66$^{4Glu}$ and BPP1'-PE40 (5 μg, total protein concentration of insoluble fraction, guanidine hydrochloride-treated), with αMBP T cells (PAS cells) or with A2b non target cells for 5 hr. At the end of the incubation, cells were washed four times with Hanks Balanced Sodium Saline (HBSS) buffer, saving samples from each washing step. Cells were then lysed with lysis buffer (20 mM Tris-HCl pH 7.4, 150 mM NaCl, 1 mM EDTA, 1% NP40, 1% deoxycholic acid, 0.1% SDS, 1 mM PMSF) and incubated for 15 min. at RT. The cell lysate was centrifuged at 9000 g for 10 min. and the pellet (dissolved in Tris-HCl pH 7.4, 1 mM EDTA, TE buffer) and supernatant fractions of the lysed cells were kept for analysis. Samples of the growing media, washing steps, and the lysed cells were applied for SDS PAGE analysis. Electrophoresed samples were transferred from gels to nitrocellulose and immunoblotted using αPE antiserum. When internalization was assayed on A2b cells, immunobloting of the samples was performed by slot-blot analysis.

After standard assay conditions, BPP2-PE66$^{4Glu}$ and BPP1'-PE40 could be detected within lysates of target cells (FIG. 10). These chimeric proteins are cell associated as samples from the last washing step (before lysing the cells, wash IV, FIG. 10) didn't reveal any immunoreactive material. No internalized chimeric proteins could be detected within the A2b non target cells under identical assay conditions (FIG. 10). As expected, chimeric proteins could be detected in this case only in the growing medium and in the first washing sample.

G. Production and Purification of BPP-PE Chimeric Proteins

MBP/BPP-PE chimeric proteins are expressed in prokaryotic systems. The expression in E. coli, as observed with many foreign eukaryotic proteins, results in the formation of insoluble inclusion bodies, which contain the recombinant protein in a non-native and non-active conformation. Further ways for obtaining the fusion proteins differ and depend on nature of its moieties.

The chimeric protein was expressed in E. coli strain BL21 (λDE3) cells. Bacterial cells were grown in SLB/Amp (50 (g/ml) (SLB in IL-5 g NaCl, 16 g tryptophan, 10 g yeast extract) medium at 37° C., until the OD$_{600}$ reached 1.5–2.0. Induction with IPTG (1 mM, 90 min. at 37° C.) resulted in the expression of the chimeric proteins. Cultures were centrifuged at 2700 rpm for 15 min. Pellets of cells were frozen at −70° C. The frozen E. coli cells were thawed and suspended in lysis buffer (50 mM Tris-HCl pH 8.0, 1 mM EDTA, 0.2 mg/ml lysozyme) (10 ml/g cells).

The cell suspension was pulse sonicated 3×30 seconds. The disrupted cells were centrifuged at 35,000×g for 30 min. at 4° C. to obtain the insoluble fraction, i.e. the inclusion bodies. The inclusion bodies were suspended in denaturing buffer (6M GuHCl, 100 mM Tris-HCl pH 8.6, 1 mM EDTA, 10 mM DTT, 50 mM NaI) (1 ml/g cells). The mixture was collected by centrifugation (35,000 g for 15 min.). Supernatant was diluted 100-fold with refolding buffer (100 mM Tris-HCl, pH 8.0, 1 mM EDTA, 0.25M Arginine, 5 mM DTT, 0.25M NaCl) and stirred for 48 hr. at 4° C.

The diluted extract was clarified by centrifugation 35,000 g for 30 min. at 4° C. Each gram of protein of the refolding solution was absorbed on to 0.7–0.8 ml of pre-treated (with BSA) hydroxyapatite. The fraction not bound to the absorbent was added with 0.25M NaCl and 100 mM arginine and concentrated with a stirrer cell (Nucleopore, membrane cut 30,000, Sigma) until final volume reached 1–2 ml. Concentrated fraction was then loaded onto a Sephacryl S-200HR column (1×120 cm) precalibrated with 50 mM K-phosphate buffer pH 7.0 and 0.25M NaCl.

Fractions of one ml were collected and tested for absorbance at 280 nm and on SDS-PAGE. Peak fractions were collected and dialyzed against PBS and designed as purified BPP1'-PE40. Highly purified BPP1'-PE40 was kept at −20° C. in aliquots.

All purification steps were followed by SDS-PAGE electrophoresis, protein measurements, Western blot analysis and ADP-ribosylation activity of the samples.

Based on total activity (as measured by ADP-ribosylation activity) a yield of 4.5% from starting material (Table III) was obtained. According to specific activity of the chimeric protein, the degree of purification was 20.8-fold (Table III).

TABLE III

Purification of BPP-PE40

| | Protein conc. mg/ml | Total protein mg | Specific activity cpm × 10$^6$/mg | Total activity cpm × 10$^6$ | Yield % | Degree of Purification |
|---|---|---|---|---|---|---|
| Whole cell extract | 5.2 | 83.2 | 12.9 | 1073 | 100 | 1 |
| Refolding solution | 0.28 | 28 | 25.3 | 708 | 66 | 2 |
| hydroxyapatite sup. | 0.022 | 2.2 | 57.6 | 127 | 12 | 4.5 |

TABLE III-continued

Purification of BPP-PE40

|  | Protein conc. mg/ml | Total protein mg | Specific activity cpm × 10⁶/ mg | Total activity cpm × 10⁶ | Yield % | Degree of Purification |
|---|---|---|---|---|---|---|
| Centricon-3 sol. | 1.15 | 1.73 | 45.4 | 78.5 | 7.3 | 3.5 |
| Sephacryl peak | 0.045 | 0.18 | 267.8 | 48 | 4.5 | 20.8 |

The highly purified chimeric protein was tested for its nonspecific toxicity. This was done by injecting a single increasing dose of chimeric protein into mice (strain SJL). Animals were observed for at least 2 weeks, although a toxic dose of PE caused death within 24–48 hours. None of the mice died at a dose of 50 µg, ⅔ of the mice died at a dose of 100 µg.

Use of an ion-exchange column (in place of the stirrer cell) after the hydroxyapatite step in the purification procedure described above, improves the purity of the end product. Fractions found not to bind to the hydroxyapatite support were diluted (1:5) with TE buffer (TE buffer: 10 mM Tris HCl pH 8.0, 1 mM EDTA), added to Q-Sepharose (5 ml of wet column media to ~20 mg protein of diluted BPP1-PE40 solution) and stirred for 30 min. at 4° C. The material was then packed into a column and washed with TE buffer. Elution was performed with 1 M NaCl in TE buffer. This step concentrated the protein samples that were then applied onto the Sephacryl column.

H. Cytotoxic Activity of Purified BPP1'-PE40

Increasing amounts of purified BPP1'-PE40 chimeric protein were added to PAS cells at day 1 (d1) of the propagation phase. As shown in FIG. 11, the highly purified BPP1'-PE40 caused inhibition of protein synthesis in a dose dependent manner.

I. Enhancement of Cytotoxicity by Lysosomotrophic Agent $NH_4Cl$ is known to be a lysosomotrophic agent which increases the lysosomal pH thus neutralizes the activity of its enzymes. Different lysosomotrophic agents such as $NH_4Cl$, monensin, etc. caused enhancement of the immunotoxins' cytotoxicity.

We examined the effect of $NH_4Cl$ on BPP1'-PE40 cytotoxicity toward target cells. As can be seen in FIG. 12, 5 mM $NH_4Cl$ dramatically increased the cytotoxic effect of BPP1'-PE40 on PAS cells. While in the absence of $NH_4CL$, 500 ng BPP1'-PE40 caused only 4% inhibition of protein synthesis, adding $NH_4Cl$ increased inhibition of protein synthesis to 98% (5 mM of $NH_4Cl$ caused in itself a 26% decrease in protein synthesis).

J. BPP-PE Cytotoxicity Toward PBL from MS Patients

Peripheral was collected from MS patients or control healthy donors. Lymphocytes were separated by application of 20 ml peripheral blood on Ficoll-isopaque (1.077). Lymphocytes were either activated with PHA (5 (g/ml) for 72 hr. or used freshly within 24 hr. Activated lymphocytes were transferred to RPMI 1640 supplemented with 10% FCS and 10 units/ml rIL2. The cytotoxic assay ($2 \times 10^4$ cells/well) was done immediately after the cells transfer. Fresh lymphocytes ($10^5$ cells/well) were maintained in the same medium as described for the T cell lines supplemented with 20% heat inactivated FCS and 10 units/ml rIL2.

Cells were seeded for protein inhibition assays that were performed on:
1) Fresh cells without any pre-activation period. Calibration experiments were performed on control fresh blood samples to ensure good availability of the cells during the assay period. Parameters such as density of cells seeded, addition of specific growth factors/cytokines, etc. were tested;
2) Cells following 2–3 days of activation PHA. In parallel experiments, control blood samples taken from healthy individuals were tested in a similar manner, examining for specificity of the chimeric proteins used.

The study was performed on MS patients mainly at relapses of the disease. Eighteen MS patients were included in this study. Fresh cells (without any pre-activation) from eleven patients were examined with BPP1'-PE40 at different stages of its purification (following the progress in the purification protocol). Peripheral blood cells from six patients (54%) were sensitive to BPP1'-PE40 mediated cytotoxicity with inhibition of protein synthesis ranging from 20% to 92%. FIG. 13 demonstrates the effect of BPP1'-PE40 on a few MS patients, one that was very sensitive to the chimera (MSM-18), one that did not show any response (MSM-16) and two other patients that showed low to moderate sensitivity to BPP1'-PE40 mediated cytotoxicity (MSM-13,14).

Samples from twelve patients (part of the patients' samples were tested both as fresh cells and after activation) were tested after 3 days of activation with PHA. Six out of the twelve samples (50%) showed sensitivity to the chimera.

Cells taken from control donors showed no or very little response to the chimera. Cells taken from a patient with another, unrelated neurological disease were also tested and found unresponsive to the cytotoxic effect of BPP1'-PE40.

K. Inhibition of EAE by BPP1'-PE40

Immunization and Treatment Protocol:

18 Female SJL mice between 8–10 wk of age were immunized in 4 footpads with mice spinal cord homogenate (0.1 mg/mice) solubilized in PBS, pH 7.4, and emulsified 1:1 in CFA (5 mg/ml *Mycobacterium tuberculosum*) in a total volume of 100 µl/mice. In addition, pertusis toxin (200 ng/200 µl/mice) was i.v. injected. Boosting was done in 48 h. later with another dose of pertusis toxin, i.v. injected (200 ng/200 µl/mice).

Treatment consisted of i.p. injection every 12 h. of BPP1'-PE40 at 5 ug/mice (based on 2.5 µg/g animal) in 0.5 ml PBS pH 7.4 or 0.5 ml PBS alone. The treatment was initiated 8 days after immunization and continued for 10 days. Grading of the severity of EAE was made every day during treatment and at least 1 month later. The scoring ranged from 1 to 6 as follows:
1=mild tail weakness, 2=tail paralysis, 3=tail paralysis and hind leg paralysis, 4=hind leg paralysis or mild fore-limb weakness, 5=quadriplegia, 6=death.

Results:

BPP1'-PE40 treated mice did not develop EAE at all (mean severity=0) and none of them died from the disease. In contrast, in the PBS control group, 6 out of 9 mice developed EAE with the peak of disease on day 14. The 6 affected mice displayed differences in severity and duration of the disease, the mean severity on day 14 being 3. In addition, one of the 6 mice in the control group died from the disease.

The treated group was followed for an additional 4 weeks and no sign of a late appearance or late relapse of the disease was observed.

L. Human Chimeric Proteins

Several additional chimeric proteins based on the human MBP pathogenic sequences were constructed. The targeting sequences in these chimeric proteins were based on peptides 84–102 and 143–168 of the human MBP (Table IVb). The short peptide sequences were synthesized on a DNA synthesizer and purified by conventional protocols. Sequences of the oligo's used for the constructs are shown in Table IVa.

TABLE IVa

Sequences of oligo's used for constructing human BPP-PE chimeric proteins

Oligo 1 (143–906):
5' TATGTTTAAAGGGGTAGATGCTCAAGGGACCCTTTCTAAAAT-
TTTTAAATTGGGAGGTAGAGATCA 3' (SEQ ID NO: 7)
Oligo 2 (143–906)
5' TATGATCTCTACCTCCCAATTTAAAAATTTTAGAAAGGGTCCC-
GAGCATCTACCCCTTTAAACA 3' (SEQ ID NO: 8)
Oligo 3 (84–906):
5' TATGGATGAAAATCCAGTAGTTCATTTTTTTAAAAATATTGTAA-
CCCCACGTACCCCACCCCA 3' (SEQ ID NO: 9)
Oligo 4 (84–906):
5' TATGGGGTGGGGTACGTGGGGTTACAATATTTTTAAAAAAATG-
AACTACTGGATTTTCATCCA 3' (SEQ ID NO: 10)
Oligo 5 (84–823):
5' TATGGATGAAAATCCAGTAGTTCATTTTTTTAAAAATATTGTAAC-
CCCACGTACCCCACCCGA 3' (SEQ ID NO: 11)
Oligo 6 (84–823):
5' AGCTTCGGGTGGGGTACGTGGGGTTACAATATTTTTTAAAAAAAT-
GAACTACTGGATTTTCATCCA 3' (SEQ ID NO: 12)
Oligo 7 (143–823):
5' TATGTTTAAAGGGGTAGATGCTCAAGGGACCCTTTCTAAAAT-
TTTTAAATTGGGAGGTAGAGATGA 3' (SEQ ID NO: 13)
Oligo 8 (143–823):
5' AGCTTCATCTCTACCTCCCAATTTAAAAATTTTAGAAAGGGTGC-
CTTGAGCATCTACCCCTTTAAACA 3' (SEQ ID NO: 14)

TABLE IVb

Amino acid sequences of the human BPP's

84–102:
5' Asn Glu Asn Pro Val Val His Phe Phe Lys Asn Ile Val Thr Pro Arg Thr Pro Pro 3' (SEQ ID NO: 15)
143–168:
5' Phe Lys Gly Val Asp Ala Gln Gly Thr Leu Ser Lys Ile Phe Lys Leu Gly Gly Arg Asp 3' (SEQ ID NO: 16)

The new chimeric proteins were constructed using gene fusion techniques. Schematic representations of the plasmids encoding the new chimeric proteins are shown in FIGS. 14a–d. The targeting sequences were cloned at the 5' end of a full length modified PE (PE66$^{4Glu}$) (FIGS. 14a,b) or to a truncated form of PE-cDNA (PE40) (FIGS. 14c,d). Both forms of the PE-cDNA had been used for constructing IL2-toxin chimeric proteins and were found to exhibit a differential activity towards human and murine freshly activated T Cells. Oligo's 1–2 were used to construct BPP$_{143-168}$-PE40; Oligo's 3–4 were used to construct BPP$_{84-102}$-PE40; Oligo's 5–6 were used to construct BPP$_{84-102}$-PE66$^{4Glu}$; and Oligo's 7–8 were used to construct BPP$_{143-168}$-PE66$^{4Glu}$.

The new chimeric cytotoxins were expressed in E. coli expression systems, similar to the production of previous MBP-PE. Expression was followed by SDS-PAGE of cell extracts (FIGS. 15a–c), by Western blot analysis using anti-PE antibodies and by measuring ADP-ribosylation activity of the expressed proteins. All new chimeric proteins were highly expressed and primarily concentrated in the insoluble fraction of the expressing cells.

These human chimeric proteins were tested on target cells such as peripheral blood from MS patients. BPP$_{84-102}$-PE66$^{4Glu}$ was tested on the cells of two MS patients (already tested before, MSM 16,18) and found to be cytotoxic (Table V). One of the patients (MSM 16) responding to the new chimeric proteins based on the human sequence did not respond before to BPP1-PE40 (guinea pig-based sequence) mediated cytotoxicity. Cells from an additional MS patient had no response to BPP$_{84-102}$-PE66$^{4Glu}$.

TABLE V

Effect of BPP$_{84-102}$ – PE66$^{4Glu}$ on PBL from MS patients

| Patient | % protein synthesis inhibition (at 500 ng) |
|---|---|
| MSM-16 | 52 |
| MSM-18 | 56 |
| MSM-22 | <5 |

REFERENCES

1) Aharoni, R., Teitelbaum, D., Arnon, R. & Puri, J. (1991) immunomodulation of experimental allergic encephalomyelitis by antibodies to the antigen-la complex. Nature 351:147–150.

2) Sharma, S. D., Nag, B., SU, X-M, Green, D., Spack, E., Clark, B. R., & Sriram, S. (1991) Antigen-specific therapy of experimental allergic encephalomyelitis by soluble class II major histocompatibility complex-peptide complexes. Proc. Natl. Acad. Sci. U.S.A. 88:11465–11469.

3) Offiner, H. Hashim, G. A., Vandenbark, A. A. (1991) T cell receptor peptide therapy triggers autoregulation of experimental encephalomyelitis. Science 251:430–432.

4) Snilek, D. E., Wraith, D. C., Hodgkinson, S., Dwivedy, S., Steinman, L. & McDevitt, H. O. (1991) A single amino acid change in a myelin basic protein peptide confers the capacity to prevent rather than induce experimental autoimmune encephalomyelitis. Proc. Natl. Acad Sci. U.S.A. 88:9633–9637.

5) Alem, J. J. (1995) Conference of advances in the understanding and treatment of Multiple Sclerosis. Cambridge, Mass. 1995.

6) Lorberboum-Galski, H., Fitzgerald, D. J. P., Chaudhary, V. K., Adhya, S. & Pastan, I. (1988) Proc. Natl. Acad. Sci. U.S.A. 85:1922–1926.

7) Ogata, M., Chaudhary, V. K, Fitzgerald, D. J. & Pastan, I. (1989) Proc. Natl. Acad. Sci. U.S.A. 86:4215–9742.

8) Siegall, C. B., Chaudhary, V. K., Fitzgerald, D. J. & Pastan, I. (1988) Proc. Natl. Acad. Sci. U.S.A. 85:9738–9742.

9) Chaudhary, V. K., Mizukarni, T., Fuerst, T. R., Fitzgerald, D. J., Moss, B., Pastan, I. & Berger, E. A. (1988) Nature 335:369–372.

10) Siegall, C. B., Chaudhary, V. K., Fitzgerald, D. J. & Pastan, I. (1989) J. Biol. Chem. 264:14256–14261.

11) Kreitman, R. J., Chaudhary, V. K, Waldmann, T., Willingham, M. C., Fitzgerald, D. J., & Pastan, I. (1990)Proc. Natl. Acad. Sci. 87:8291–8295.

12) Waldmann, T. A. (1995)Immunol. Today 14:264–270.

13) Wall, J. R., Baur, R., Shlesener, H. & Bandy-Dafoe P. (1983) *J. Clin. Edocrinol. Metab.* 56:164–168.

14) Bottazo, G. F., Dean, B. M., McNally, J. M., Mackay, E. H., Swift, P. G., & Gamble, D. R. (1985) *N. Engl. J. Med.* 313:353–360.

15) Lemm, G., & Warmatz, H. (1986) *Clin. Exp. Immunol.* 64:71–79.

16) Selby, W. S., Janossy, G., Bosil, M. & Jewel, D. P. (1984) *Gut* 25:32–40.

17) Gery, I., Mochizuki, M. & Nussenblatt, R. B. (1986) *In Progress in Retinol. Research eds.* Osborne, N. and Chader, Y. (Pergamon, Oxford and New York) pp. 75–109.

18) Shapiro, M. E., Kirkman, R. L., Reed, M. H., Puskas, J. D., Mazoiyian, G., Letvin, N. L., Carpenter, C. B., Milford, E. L., Waldmann, T. A. & Strom, T. B. (1987) *Transplant Proc.* 19:594–598.

19) Heidecke, C. D., Kupiec-Welylinki, J. W., Lear, P. A., Abbud-Filho, M., Araujo, J. L., Araneda, D., Strom, T. B. & Tilney, N. L. (1984) *J. Immunol.* 133:582–588.

20) Bailon, P., Weber, D. V., Gately, M., Smart, J. E., Lorberboum-Galski, H., Fitzgerald, D. & Pastan, I. (1988) *Biotechnol.* 6:1326–1929.

21) Case, J. P., Lorberboum-Galski, H., Lafyatis, R., Fitzgerald, D., Wilder, R. L. & Pastan, I. (1989) Chimeric cytotoxin IL2-PE40 prevents adjuvant arthritis in rats. *Proc. Natl. Acad. Sci U.S.A.* 86:287–291.

22) Lorberboumr-Galski, H., Barret, L., Kirkman, R., Ogata, M., Willingham, M., Fitzgerald, D; & Pastan, I. (1989) Cardiac allograft survival in mice treated with IL2-PE40. *Proc. Natl. Acad. Sci U.S.A.* 86:1008–1012.

23) Roberge, F. G., Lorberboum-Galsid, H., Phoan, P. L., desmet, M., Chan, C. C., Fitzgerald, D & Pastan, I. (1989) Selective immunosuppression of activited T cells with the chimeric toxin IL2-PE40: Inhibition of experimental autoimmune uveoretinitis (EAU). *J. Immunol.* 143:3498–3502.

24) Kozak, R. W., Lorberboum-Galski, H., Jones, L., Puri, R. J. K., Willingham, M. C., Malek, T., Fitzgerald, D. J., Waldman, T. a. & Pastan, I. (1990) *J. Immunol.* 145:2766–2771.

25) Herbort, C. P., deSmet, M. D., Roberge, F. G., Nussenblatt, R. B., Fitzgerald, D., Lorbergboum-Galski, H., & Pastan, I. (1991) *Transplantation* 52:470–474.

26) Beraud, E., Lorberboum-Galski,H., Chan, C. C., Fitzgerald, D., Pastan, I. & Nussenblatt, R. B. (1991) Immunospecific Suppression of encephalitogenic activated T lymphocytes by chimeric eytotoxin IL2-PE40. *CellularImmunol.* 133:379–389.

27) Rose, J. W., Lorberboum-Galski H., Fitzgerald, D., McCarron, R., Hill, K. E., Townsend, J. J. & Psatan, I. (1991) Chimeric cytotoxin IL2-PE40 inhibitis relapsing experimental allelic encephalmyelitits. *J. Neuroimmunol.* 32:209–217.

28) Lorberboum-Galsky, H., Garsia, R. J., Gately, M., Brown, P. S., Clark, R. R., Waldmann, T. A., Fitzgerald, D. J. P. & Pastan, I. (1990) IL2-PE66 $^{4Glu}$:A new chimeric protein cytotoxic to human activated T lymphocytes. *J. Biol. Chem.* 265:16311–16317.

29) Kibler, R. F., Fritz, R. B., Chou, F, C-H, Chou, J., Peacocke, N., Brown, N. M. & McFarlin, D. E. (1977) Immune response of Lewis rats to peptide C1 (Residues 68–88) of guinea pig and ray myelin basic proteins. *J. Exp. Med.* 146:1323–1331.

29a) Ota, K. M.m Matsui, E. L., Milford, G. A., Mackin, H. L., Weiner and Hafler D. A. (1990) *Nature* 346, 183.

29b) Fishman, A., Bar-kana, Y., Steinberger, I. and Lorberboum, Galski, H. (1994), *Biochemistry*, 6235–6243.

30) Roach, A., Boylan, D., Horrath, S. Prusiner, S. B. & Hood. L. E., (1983) *Cell* 34:799–806.

31) Collier, R. J. & Kandel, J. (1971) *J. Biol. Chem.* 256:1496–1503.

32) Maniatis T et al(1982), "Molecular Cloning, A Laboratory Manual".

It will be appreciated by persons skilled in the art that the present invention is not limited to what has been thus far described, but rather the scope of the present invention is limited only by the following claims:

---

What is claimed is:

1. A chimeric protein, consisting of a *Pseudomonas aeruginosa* exotoxin (PE) moiety as a cytotoxic agent linked to a myelin basic protein (MBP) moiety selected from the group consisting of:

(a) amino acids 69–88 of guinea-pig myelin basic protein, encoded by nucleotides 8–64 of SEQ ID NO:1, or an antigenic portion thereof recognizing anti-MBP specific T-cells;

(b) amino acids 84–102 (SEQ ID NO:15) of human myelin basic protein or an antigenic portion thereof recognizing anti-MBP specific T-cells; and (c) amino acids 143–168 (SEQ ID NO:16) of human myelin basic protein or an antigenic portion thereof recognizing anti-MBP specific T-cells, wherein one of said MBP amino acid sequences (a), (b) and (c) is linked to said PE moiety by a pentapeptide or by a peptide consisting of said pentapeptide repeated twice.

2. The protein according to claim 1, wherein said PE moiety comprises PE mutated at one or more of amino acid positions 57, 246, 247, and 249.

3. The protein according to claim 1, wherein said PE moiety comprises domains II and III of the exotoxin.

4. A pharmaceutical composition comprising the chimeric protein as defined in claim 1 and an inert carrier.

5. The pharmaceutical composition according to claim 4, further comprising a lysosomotrophic agent.

6. The protein according to claim 1, wherein said MBP moiety is amino acids 69–88 of guinea-pig myelin basic protein or an antigenic portion thereof recognizing anti-MBP specific T-cells.

7. The protein according to claim 1, wherein said MBP moiety is amino acids 84–102 (SEQ ID NO:15) of human myelin basic protein or an antigenic portion thereof recognizing anti-MBP specific T-cells.

8. The protein according to claim 1, wherein said,MBP moiety is amino acids 143–168 (SEQ ID NO:16) of human myelin basic protein or an antigenic portion thereof recognizing anti-MBP specific T-cells.

9. The protein according to claim 1, wherein said pentapeptide comprises the amino acid sequence gly-gly-gly-gly-ser (SEQ ID NO:17)).

10. An isolated DNA sequence encoding the chimeric protein according to claim 1.

11. A plasmid comprising a promoter operatively linked to the DNA sequence according to claim 10.

12. An expression vector capable of expressing the protein according to claim 10, comprising a plasmid which comprises a promoter operatively linked to the DNA sequence encoding the protein.

13. A method for treating multiple sclerosis, comprising administering to a patient in need thereof an effective amount of a pharmaceutical composition according to claim 4 to eliminate anti-MBP specific T-cells and to treat multiple sclerosis.

14. A method for treating multiple sclerosis, comprising administering to a patient in need thereof an effective amount of a pharmaceutical composition according to claim 5 to eliminate anti-MBP specific T-cells and to treat multiple sclerosis.

* * * * *